United States Patent
Arnaud et al.

(10) Patent No.: US 9,572,764 B2
(45) Date of Patent: Feb. 21, 2017

(54) COMPOSITION COMPRISING PERLITE AND A POLYMER BEARING A CARBOSILOXANE DENDRIMER-BASED UNIT

(75) Inventors: Pascal Arnaud, L'hay les Roses (FR); Amanda Chen, Shanghai (CN); Anne-Catherine Legros, Cernay la Ville (FR)

(73) Assignee: L'OREAL, Paris (FR)

( * ) Notice: Subject to any disclaimer, the term of this patent is extended or adjusted under 35 U.S.C. 154(b) by 450 days.

(21) Appl. No.: 14/007,828

(22) PCT Filed: Mar. 30, 2012

(86) PCT No.: PCT/EP2012/055908
§ 371 (c)(1),
(2), (4) Date: Dec. 16, 2013

(87) PCT Pub. No.: WO2012/131083
PCT Pub. Date: Oct. 4, 2012

(65) Prior Publication Data
US 2014/0127274 A1 May 8, 2014

Related U.S. Application Data

(60) Provisional application No. 61/476,784, filed on Apr. 19, 2011.

(30) Foreign Application Priority Data

Apr. 1, 2011 (FR) ...................................... 11 52807

(51) Int. Cl.
| | | |
|---|---|---|
| A61K 8/02 | (2006.01) |
| A61K 8/91 | (2006.01) |
| A61K 8/19 | (2006.01) |
| A61K 8/25 | (2006.01) |
| A61K 8/26 | (2006.01) |
| A61K 8/895 | (2006.01) |
| A61K 8/896 | (2006.01) |
| A61Q 1/02 | (2006.01) |
| A61Q 1/00 | (2006.01) |
| A61Q 19/00 | (2006.01) |

(52) U.S. Cl.
CPC . *A61K 8/91* (2013.01); *A61K 8/19* (2013.01); *A61K 8/25* (2013.01); *A61K 8/26* (2013.01); *A61K 8/895* (2013.01); *A61K 8/896* (2013.01); *A61Q 1/00* (2013.01); *A61Q 1/02* (2013.01); *A61Q 19/00* (2013.01); *A61Q 19/008* (2013.01)

(58) Field of Classification Search
CPC ....................................................... A61K 8/91
See application file for complete search history.

(56) References Cited

U.S. PATENT DOCUMENTS

2011/0171151 A1* 7/2011 Arnaud .................... A61K 8/25
424/63

FOREIGN PATENT DOCUMENTS

| EP | 1862162 A1 | 12/2007 | |
|---|---|---|---|
| FR | 2881643 A1 | 8/2006 | |
| FR | 2924929 A1 | 6/2009 | |
| FR | 2935268 A1 | 3/2010 | |
| FR | 2935269 A1 | 3/2010 | |
| FR | WO 2010054921 A1 * | 5/2010 | ........... A61K 8/0229 |

* cited by examiner

*Primary Examiner* — Paul Dickinson
(74) *Attorney, Agent, or Firm* — Polsinelli PC

(57) ABSTRACT

The present invention concerns a composition comprising a physiologically acceptable medium containing perlite and at least one vinyl polymer bearing at least one carbosiloxane dendrimer-based unit. The composition is used in the care of and for making up the skin, in particular to provide a matt effect.

19 Claims, No Drawings

COMPOSITION COMPRISING PERLITE AND A POLYMER BEARING A CARBOSILOXANE DENDRIMER-BASED UNIT

CROSS REFERENCE TO RELATED APPLICATIONS

This application is a National Phase filing under 35 U.S.C. §371 of PCT/EP2012/055908 filed on Mar. 30, 2012; and this application claims priority to Application No. 1152807 filed in France on Apr. 1, 2011; which claims the benefit of U.S. Provisional Application No. 61/476,784 filed on Apr. 19, 2011; the entire contents of all are hereby incorporated by reference.

The present invention relates to compositions for caring for and/or making up the skin. More particularly, the present invention relates to compositions for giving the skin a matt effect and which have improved remanence of this matt effect over time.

Cosmetic compositions, for instance foundations, are commonly used to give the skin, especially the face, a colour and an aesthetic effect. These makeup products generally contain oils, pigments, fillers and optionally additives such as cosmetic or dermatological active agents.

It is known to those skilled in the art to use fillers in order to obtain a matt effect. These fillers are usually chosen as a function of their sebum-absorbing properties and/or their light-scattering capacities. However, their adhesion to the skin is generally poor, especially in the presence of sebum.

Film-forming polymers may then be used to improve the adhesion of these fillers, and to increase the remanence of the matt effect throughout the day.

These polymers are of very different chemical nature and may be conveyed in the fatty phase or in the aqueous phase. Examples of these polymers that may be mentioned include silicone resins, polyacrylates and latices.

Thus, U.S. Pat. No. 6,887,859 describes skincare and skin makeup compositions containing a combination of film-forming polymers and fillers.

Although these formulations do indeed make it possible to give cosmetic compositions certain matting-remanence properties, they may, however, be accompanied by unpleasant sensations and discomfort either during the application of the product (difficulty in spreading, tacky effect, greasy feel, etc.) or in the course of the day (tautness, mask effect, etc.).

FR 2 878 738 and EP 1 862 162 also describe cosmetic compositions comprising a vinyl polymer comprising carbosiloxane dendrimer-based units and fillers.

There is thus still a need for cosmetic compositions that have a matt effect and improved remanence of the matt effect, which are pleasant and easy to apply, while at the same time maintaining satisfactory comfort on application i.e. not causing any sensation of tautness or mask effect throughout the day and/or not inducing any greasy or tacky sensation during their application.

The object of the present invention is to satisfy these needs.

The aim of the present invention is thus to provide a cosmetic composition with a good compromise between the matt effect and the remanence over time of this matt effect, while at the same time maintaining satisfactory comfort on application.

The present invention concerns a composition comprising a physiologically acceptable medium containing perlite and at least one vinyl polymer bearing at least one carbosiloxane dendrimer-based unit.

The compositions according to the invention are cosmetic compositions for caring for and/or making up the skin.

The inventors have observed, unexpectedly, that the introduction into a skincare and/or skin makeup composition of a vinyl polymer bearing at least one carbosiloxane dendrimer-based unit in combination with perlite gives these compositions very good remanence of the matt effect, while at the same time maintaining satisfactory comfort on application. What is more, these compositions remain pleasant to wear throughout the day.

Hitherto, it had never been demonstrated that a combination of a polymer and perlite in accordance with the invention makes it possible to give cosmetic compositions a matt effect and improved remanence of the matt effect while at the same time giving very satisfactory sensations of comfort on application of the composition and during its use throughout the day.

Vinyl Polymer Grafted with a Carbosiloxane Dendrimer

A vinyl polymer that is suitable for preparing a composition according to the invention comprises at least one carbosiloxane dendrimer-based unit.

The vinyl polymer has a backbone and at least one side chain, which comprises a carbosiloxane dendrimer-based unit having a carbosiloxane dendrimer structure.

The term "carbosiloxane dendrimer structure" in the context of the present invention represents a structure with branched groups of high molecular masses, the said structure having high regularity in the radial direction starting from the bond to the backbone. Such carbosiloxane dendrimer structures are described in the form of a highly branched siloxane-silylalkylene copolymer in the laid-open Japanese patent application Kokai 9-171 154.

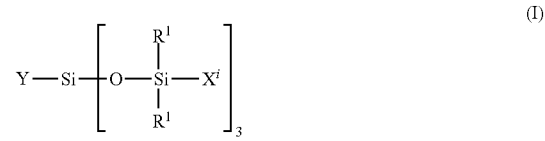

(I)

A vinyl polymer according to the invention may contain carbosiloxane dendrimer-based units that may be represented by the general formula (I) below:

in which:
$R^1$ represents an aryl group of 5 to 10 carbon atoms or an alkyl group of 1 to 10 carbon atoms;
$X^i$ represents a silylalkyl group which, when i=1, is represented by formula (II):

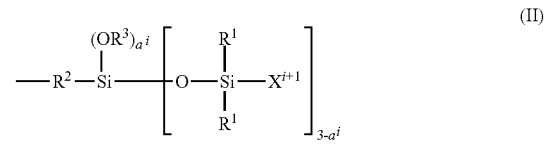

(II)

in which:
$R^1$ is as defined above in formula (I),
$R^2$ represents an alkylene radical of 2 to 10 carbon atoms,
$R^3$ represents an alkyl group of 1 to 10 carbon atoms, $X^{i+1}$ is chosen from: a hydrogen atom, an alkyl group of 1 to 10 carbon atoms, an aryl group of 5 to 10 carbon atoms and a silylalkyl group defined above of formula (II) with i=i+1.

i is an integer from 1 to 10 which represents the generation of the said silylalkyl group, and $a^i$ is an integer from 0 to 3;

Y represents a radical-polymerizable organic group chosen from:

organic groups containing a methacrylic group or an acrylic group, the said organic groups being represented by the formulae:

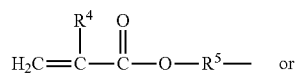

or

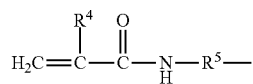

in which:

$R^4$ represents a hydrogen atom or an alkyl group of 1 to 10 carbon atoms; and $R^5$ represents an alkylene group of 1 to 10 carbon atoms, such as a methylene group, an ethylene group, a propylene group or a butylene group, methylene and propylene groups being preferred; and organic groups containing a styryl group of formula:

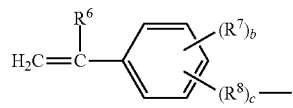

in which:

$R^6$ represents a hydrogen atom or an alkyl group of 1 to 10 carbon atoms, such as a methyl group, an ethyl group, a propyl group or a butyl group, the methyl group being preferred;

$R^7$ represents an alkyl group of 1 to 10 carbon atoms;

$R^8$ represents an alkylene group of 1 to 10 carbon atoms, such as a methylene group, an ethylene group, a propylene group or a butylene group, the ethylene group being preferred;

b is an integer from 0 to 4; and c is 0 or 1, such that if c is 0, $—(R^8)_c—$ represents a bond.

According to one embodiment, $R^1$ may represent an aryl group containing from 5 to 10 carbon atoms or an alkyl group containing from 1 to 10 carbon atoms. The alkyl group may preferably be represented by a methyl group, an ethyl group, a propyl group, a butyl group, a pentyl group, an isopropyl group, an isobutyl group, a cyclopentyl group or a cyclohexyl group. The aryl group may preferably be represented by a phenyl group and a naphthyl group. The methyl and phenyl groups are more particularly preferred, and the methyl group is preferred among all.

According to one embodiment, $R^2$ represents an alkylene group containing from 2 to 10 carbon atoms, especially a linear alkylene group, such as an ethylene, propylene, butylene or hexylene group; or a branched alkylene group, such as a methylmethylene, methylethylene, 1-methylpentylene or 1,4-dimethylbutylene group.

The ethylene, methylethylene, hexylene, 1-methylpentylene and 1,4-dimethylbutylene groups are preferred among all.

According to one embodiment, $R^3$ is chosen from methyl, ethyl, propyl, butyl and isopropyl groups.

In formula (II), i indicates the generation number and thus corresponds to the number of repetitions of the silylalkyl group.

For example, when the generation number is equal to 1, the carbosiloxane dendrimer may be represented by the general formula shown below, in which Y, $R^1$, $R^2$ and $R^3$ are the same as defined above, $R^{12}$ represents a hydrogen atom or is identical to $R^1$; $a^1$ is identical to $a^i$. Preferably, the total mean number of groups $OR^3$ in a molecule is within the range from 0 to 7.

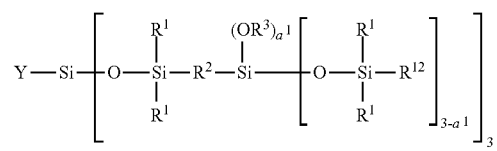

When the generation number is equal to 2, the carbosiloxane dendrimer may be represented by the general formula below, in which Y, $R^1$, $R^2$, $R^3$ and $R^{12}$ are the same as defined above; $a^1$ and $a^2$ represent the $a^i$ of the indicated generation. Preferably, the total mean number of groups $OR^3$ in a molecule is within the range from 0 to 25.

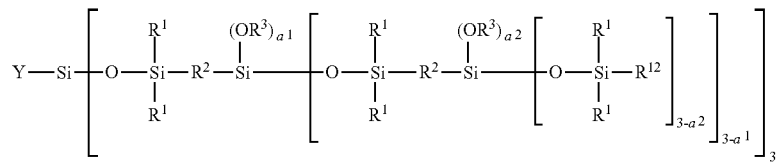

When the generation number is equal to 3, the carbosiloxane dendrimer is represented by the general formula below, in which Y, $R^1$, $R^2$, $R^3$ and $R^{12}$ are the same as defined above; $a^1$, $a^2$ and $a^3$ represent the $a^i$ of the indicated generation. Preferably, the total mean number of groups $OR^3$ in a molecule is within the range from 0 to 79.

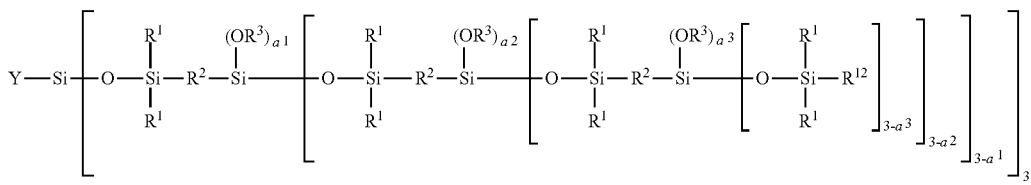

A vinyl polymer containing at least one carbosiloxane dendrimer-based unit has a molecular side chain containing a carbosiloxane dendrimer structure, and may be the product of polymerization of:
(A) from 0 to 99.9 parts by weight of a vinyl monomer; and
(B) from 100 to 0.1 part by weight of a carbosiloxane dendrimer containing a radical-polymerizable organic group, represented by the general formula (I) as defined above.

The monomer of vinyl type that is the component (A) in the vinyl polymer bearing at least one carbosiloxane dendrimer-based unit is a monomer of vinyl type that contains a radical-polymerizable vinyl group.

There is no particular limitation as regards such a monomer.

The following are examples of this monomer of vinyl type: methyl methacrylate, ethyl methacrylate, n-propyl methacrylate, isopropyl methacrylate or a methacrylate of a lower alkyl analogue; glycidyl methacrylate; butyl methacrylate, butyl acrylate, n-butyl methacrylate, isobutyl methacrylate, tert-butyl acrylate, tert-butyl methacrylate, n-hexyl methacrylate, cyclohexyl methacrylate, 2-ethylhexyl acrylate, 2-ethylhexyl methacrylate, octyl methacrylate, lauryl methacrylate, stearyl acrylate, stearyl methacrylate or a higher-analogue methacrylate; vinyl acetate, vinyl propionate or a vinyl ester of a lower fatty acid analogue; vinyl caproate, vinyl 2-ethylhexoate, vinyl laurate, vinyl stearate or an ester of a higher fatty acid analogue; styrene, vinyltoluene, benzyl methacrylate, phenoxyethyl methacrylate, vinylpyrrolidone or similar vinylaromatic monomers; methacrylamide, N-methylolmethacrylamide, N-methoxymethylmethacrylamide, isobutoxymethoxymethacrylamide, N,N-dimethylmethacrylamide or similar monomers of vinyl type containing amide groups; hydroxyethyl methacrylate, hydroxypropyl methacrylate or similar monomers of vinyl type containing hydroxyl groups; acrylic acid, methacrylic acid, itaconic acid, crotonic acid, fumaric acid, maleic acid or similar monomers of vinyl type containing a carboxylic acid group; tetrahydrofurfuryl methacrylate, butoxyethyl methacrylate, ethoxydiethylene glycol methacrylate, polyethylene glycol methacrylate, polypropylene glycol monomethacrylate, hydroxybutyl vinyl ether, cetyl vinyl ether, 2-ethylhexyl vinyl ether or a similar monomer of vinyl type with ether bonds; methacryloxypropyltrimethoxysilane, polydimethylsiloxane containing a methacrylic group on one of its molecular ends, polydimethylsiloxane containing a styryl group on one of its molecular ends, or a similar silicone compound containing unsaturated groups; butadiene; vinyl chloride; vinylidene chloride; methacrylonitrile; dibutyl fumarate; anhydrous maleic acid; anhydrous succinic acid; methacryl glycidyl ether; an organic salt of an amine, an ammonium salt, and an alkali metal salt of methacrylic acid, of itaconic acid, of crotonic acid, of maleic acid or of fumaric acid; a radical-polymerizable unsaturated monomer containing a sulfonic acid group such as a styrenesulfonic acid group; a quaternary ammonium salt derived from methacrylic acid, such as 2-hydroxy-3-methacryloxypropyltrimethylammonium chloride; and a methacrylic acid ester of an alcohol containing a tertiary amine group, such as a methacrylic acid ester of diethylamine.

Multifunctional monomers of vinyl type may also be used.

The following are examples of such compounds: trimethylolpropane trimethacrylate, pentaerythrityl trimethacrylate, ethylene glycol dimethacrylate, tetraethylene glycol dimethacrylate, polyethylene glycol dimethacrylate, 1,4-butanediol dimethacrylate, 1,6-hexanediol dimethacrylate, neopentyl glycol dimethacrylate, trimethylolpropanetrioxyethyl methacrylate, tris(2-hydroxyethyl)isocyanurate dimethacrylate, tris(2-hydroxyethyl)isocyanurate trimethacrylate, polydimethylsiloxane capped with styryl groups containing divinylbenzene groups on both ends, or similar silicone compounds containing unsaturated groups.

A carbosiloxane dendrimer, which is the component (B), may be represented by formula (I) as defined above.

The following are the preferred examples of group Y of formula (I): an acryloxymethyl group, a 3-acryloxypropyl group, a methacryloxymethyl group, a 3-methacryloxypropyl group, a 4-vinylphenyl group, a 3-vinylphenyl group, a 4-(2-propenyl)phenyl group, a 3-(2-propenyl)phenyl group, a 2-(4-vinylphenyl)ethyl group, a 2-(3-vinylphenyl)ethyl group, a vinyl group, an allyl group, a methallyl group and a 5-hexenyl group.

A carbosiloxane dendrimer according to the present invention may be represented by the following average structural formulae:

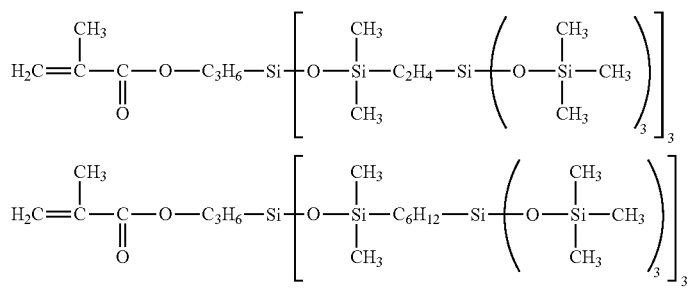

-continued
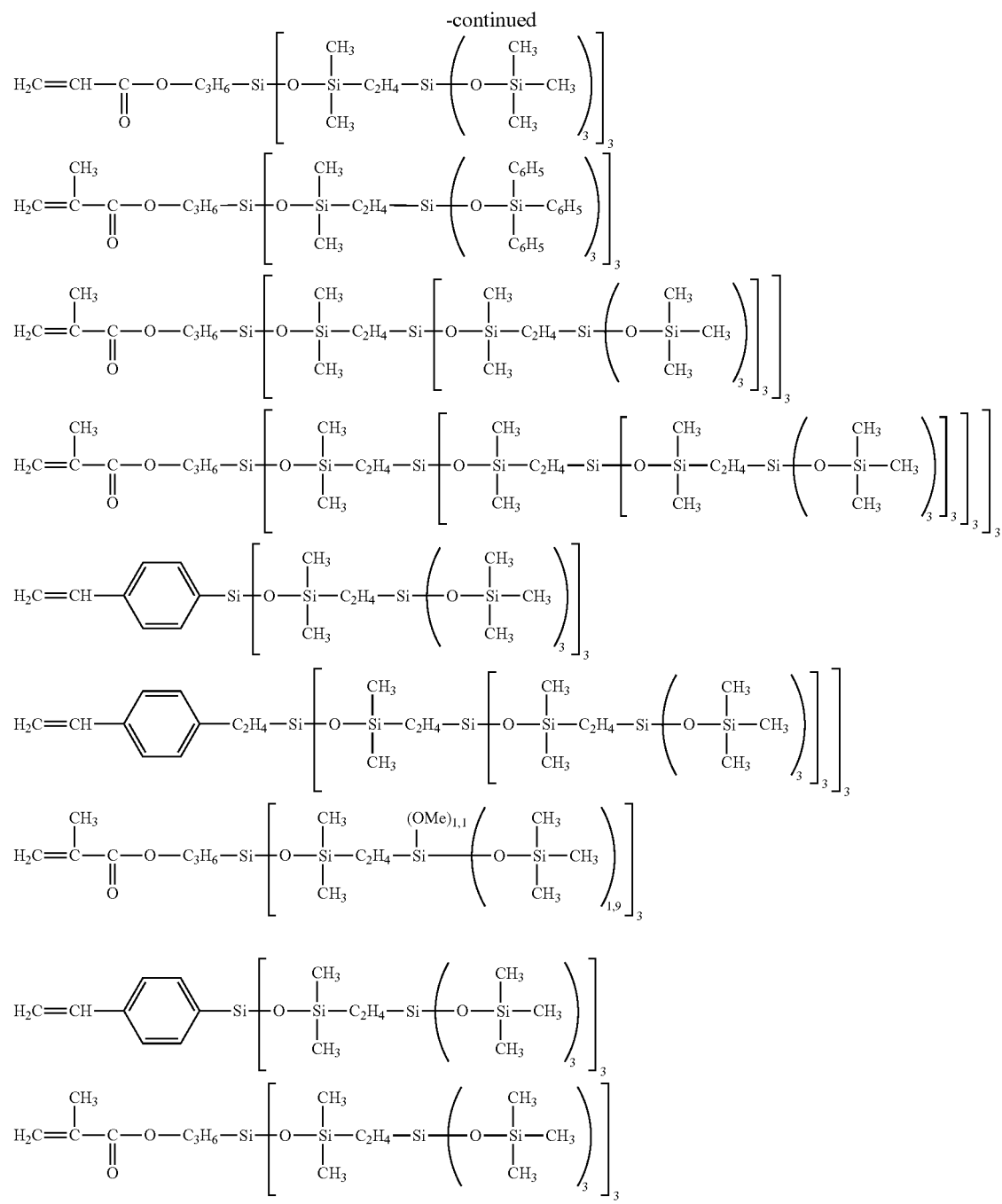
Thus, according to one embodiment, the carbosiloxane dendrimer of the composition according to the present invention is represented by the following formula:
in which:
Y, $R^1$, $R^2$ and $R^3$ are as defined above in formulae (I) and (II);
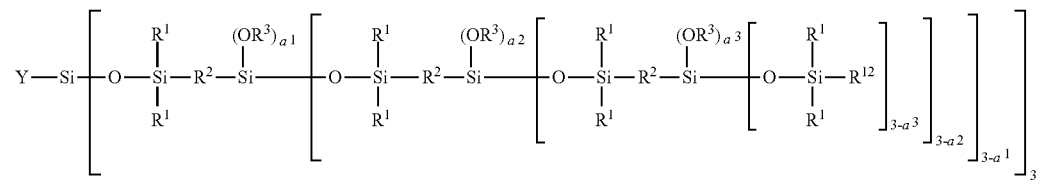

$a^1$, $a^2$ and $a^3$ correspond to the definition of $a^i$ according to formula (II); and $R^{12}$ is H, an aryl group of 5 to 10 carbon atoms or an alkyl group of 1 to 10 carbon atoms.

According to one embodiment, the carbosiloxane dendrimer of the composition according to the present invention is represented by one of the following formulae:

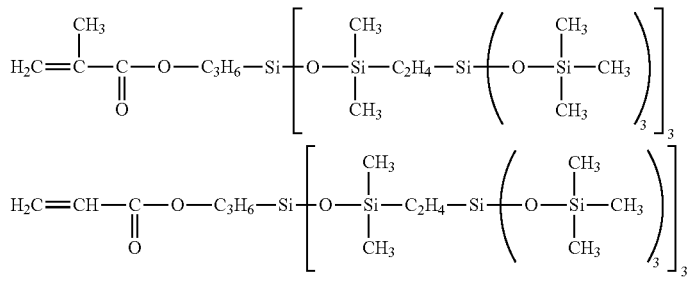

The vinyl polymer comprising the carbosiloxane dendrimer according to the invention may be manufactured according to the process for manufacturing a branched silalkylene siloxane described in Japanese patent application Hei 9-171 154.

For example, it may be produced by subjecting to a hydrosilylation reaction an organosilicon compound containing a hydrogen atom linked to a silicon atom, represented by the general formula (IV) below:

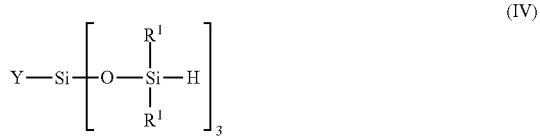

(IV)

$R^1$ being as defined above in formula (I), and an organosilicon compound containing an alkenyl group, to a hydrosilylation reaction.

In the above formula, the organosilicon compound may be represented by 3-methacryloxypropyltris(dimethylsiloxy)silane, 3-acryloxypropyltris(dimethylsiloxy)silane and 4-vinylphenyltris(dimethylsiloxy)silane. The organosilicon compound that contains an alkenyl group may be represented by vinyltris(trimethylsiloxy)silane, vinyltris(dimethylphenylsiloxy)silane, and 5-hexenyltris(trimethylsiloxy)silane.

The hydrosilylation reaction is performed in the presence of a chloroplatinic acid, a complex of vinylsiloxane and of platinum, or a similar transition metal catalyst.

A vinyl polymer containing at least one carbosiloxane dendrimer-based unit may be chosen from polymers such that the carbosiloxane dendrimer-based unit is a carbosiloxane dendritic structure represented by formula (III):

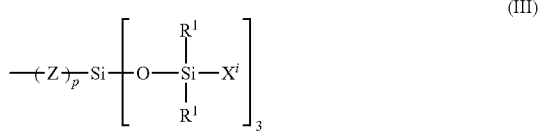

(III)

in which Z is a divalent organic group, p is 0 or 1, $R^1$ is as defined above in formula (IV) and $X^i$ is a silylalkyl group represented by formula (II) as defined above.

In a vinyl polymer containing at least one carbosiloxane dendrimer-based unit, the polymerization ratio between the components (A) and (B), in terms of the weight ratio between (A) and (B), is within a range from 0/100 to 99.9/0.1, or even from 0.1/99.9 to 99.9/0.1 and preferably within a range from 1/99 to 99/1. A ratio between the components (A) and (B) of 0/100 means that the compound becomes a homopolymer of component (B).

A vinyl polymer containing at least one carbosiloxane dendrimer-based unit may be obtained by copolymerization of the components (A) and (B), or by polymerization of the component (B) alone.

The polymerization may be a free-radical polymerization or an ionic polymerization, but free-radical polymerization is preferred.

The polymerization may be performed by bringing about a reaction between the components (A) and (B) in a solution for a period of from 3 to 20 hours in the presence of a radical initiator at a temperature of from 50° C. to 150° C.

A suitable solvent for this purpose is hexane, octane, decane, cyclohexane or a similar aliphatic hydrocarbon; benzene, toluene, xylene or a similar aromatic hydrocarbon; diethyl ether, dibutyl ether, tetrahydrofuran, dioxane or ethers; acetone, methyl ethyl ketone, methyl isobutyl ketone, diisobutyl ketone or similar ketones; methyl acetate, ethyl acetate, butyl acetate, isobutyl acetate or similar esters; methanol, ethanol, isopropanol, butanol or similar alcohols; octamethylcyclotetrasiloxane, decamethylcyclopentasiloxane, hexamethyldisiloxane, octamethyltrisiloxane or a similar organosiloxane oligomer.

A radical initiator may be any compound known in the art for standard free-radical polymerization reactions. The specific examples of such radical initiators are 2,2'-azobis(isobutyronitrile), 2,2'-azobis(2-methylbutyronitrile), 2,2'-azobis(2,4-dimethylvaleronitrile) or similar compounds of azobis type; benzoyl peroxide, lauroyl peroxide, tert-butyl peroxybenzoate, tert-butyl peroxy-2-ethylhexanoate or a similar organic peroxide. These radical initiators may be used alone or in a combination of two or more. The radical initiators may be used in an amount of from 0.1 to 5 parts by weight per 100 parts by weight of the components (A) and (B). A chain-transfer agent may be added. The chain-transfer agent may be 2-mercaptoethanol, butyl mercaptan, n-dodecyl mercaptan, 3-mercaptopropyltrimethoxysilane, a polydimethylsiloxane containing a mercaptopropyl group or a similar compound of mercapto type; methylene chloride, chloroform, carbon tetrachloride, butyl bromide, 3-chloropropyltrimethoxysilane or a similar halogenated compound.

In the manufacture of the polymer of vinyl type, after the polymerization, the residual unreacted vinyl monomer may be removed under conditions of heating under vacuum.

To facilitate the preparation of the starting material for the cosmetic products, the number-average molecular mass of the vinyl polymer that contains a carbosiloxane dendrimer may be chosen in the range between 3000 and 2 000 000 and preferably between 5000 and 800 000. It may be a liquid, a gum, a paste, a solid, a powder or any other form. The preferred forms are solutions consisting of the dilution of a dispersion or of a powder in solvents.

The vinyl polymer may be a dispersion of a polymer of vinyl type having a carbosiloxane dendrimer structure in its side molecular chain, in a liquid such as a silicone oil, an organic oil, an alcohol or water.

The silicone oil may be a dimethylpolysiloxane with the two molecular ends capped with trimethylsiloxy groups, a copolymer of methylphenylsiloxane and of dimethylsiloxane having the two molecular ends capped with trimethylsiloxy groups, a copolymer of methyl-3,3,3-trifluoropropylsiloxane and of dimethylsiloxane having the two molecular ends capped with trimethylsiloxy groups, or similar unreactive linear silicone oils, and also hexamethylcyclotrisiloxane, octamethylcyclotetrasiloxane, decamethylcyclopentasiloxane, dodecamethylcyclohexasiloxane or a similar cyclic compound. In addition to the unreactive silicone oils, modified polysiloxanes containing functional groups such as silanol groups, amino groups and polyether groups on the ends or within the side molecular chains may be used.

The organic oils may be isododecane, liquid paraffin, isoparaffin, hexyl laurate, isopropyl myristate, myristyl myristate, cetyl myristate, 2-octyldodecyl myristate; isopropyl palmitate, 2-ethylhexyl palmitate, butyl stearate, decyl oleate, 2-octyldodecyl oleate, myristyl lactate, cetyl lactate, lanolin acetate, stearyl alcohol, cetostearyl alcohol, oleyl alcohol, avocado oil, almond oil, olive oil, cocoa oil, jojoba oil, gum oil, sunflower oil, soybean oil, camellia oil, squalane, castor oil, cottonseed oil, coconut oil, egg yolk oil, polypropylene glycol monooleate, neopentyl glycol 2-ethylhexanoate or a similar glycol ester oil; triglyceryl isostearate, the triglyceride of a fatty acid of coconut oil, or a similar oil of a polyhydric alcohol ester; polyoxyethylene lauryl ether, polyoxypropylene cetyl ether or a similar polyoxyalkylene ether.

The alcohol may be any type that is suitable for use in combination with a cosmetic product starting material. For example, it may be methanol, ethanol, butanol, isopropanol or similar lower alcohols.

A solution or a dispersion of the alcohol should have a viscosity within the range from 10 to $10^9$ mPa at 25° C. To improve the sensory use properties in a cosmetic product, the viscosity should be within the range from 100 to $5 \times 10^8$ mPa·s.

The solutions and dispersions may be readily prepared by mixing the vinyl polymer having a carbosiloxane dendrimer structure with a silicone oil, an organic oil, an alcohol or water. The liquids may be present in the polymerization step. In this case, the unreacted residual vinyl monomer should be completely removed by heat treatment of the solution or dispersion under atmospheric pressure or reduced pressure.

In the case of a dispersion, the dispersity of the polymer of vinyl type may be improved by adding a surfactant.

Such an agent may be hexylbenzenesulfonic acid, octylbenzenesulfonic acid, decylbenzenesulfonic acid, dodecylbenzenesulfonic acid, cetylbenzenesulfonic acid, myristylbenzenesulfonic acid or anionic surfactants of the sodium salts of these acids; octyltrimethylammonium hydroxide, dodecyltrimethylammonium hydroxide, hexadecyltrimethylammonium hydroxide, octyldimethylbenzylammonium hydroxide, decyldimethylbenzylammonium hydroxide, dioctadecyldimethylammonium hydroxide, beef tallow-trimethylammonium hydroxide, coconut oil-trimethylammonium hydroxide, or a similar cationic surfactant; a polyoxyalkylene alkyl ether, a polyoxyalkylenealkylphenol, a polyoxyalkylene alkyl ester, the sorbitol ester of polyoxyalkylene, polyethylene glycol, polypropylene glycol, an ethylene oxide additive of diethylene glycol trimethylnonanol, and nonionic surfactants of polyester type, and also mixtures.

In the dispersion, a mean particle diameter of the polymer of vinyl type may be within a range of between 0.001 and 100 microns and preferably between 0.01 and 50 microns. The reason for this is that, outside the recommended range, a cosmetic product mixed with the emulsion will not have a nice enough feel on the skin or to the touch, or sufficient spreading properties or a pleasant feel.

A vinyl polymer contained in the dispersion or the solution may have a concentration in the range between 0.1% and 95% by weight and preferably between 5% and 85% by weight. However, to facilitate the handling and the preparation of the mixture, the range should preferably be between 10% and 75% by weight.

A vinyl polymer that is suitable for use in the invention may also be one of the polymers described in the examples of patent application EP 0 963 751.

According to one preferred embodiment, a vinyl polymer grafted with a carbosiloxane dendrimer may be the product of polymerization of:

(A1) from 0 to 99.9 parts by weight of one or more acrylate or methacrylate monomers; and (B1) from 100 to 0.1 part by weight of an acrylate or methacrylate monomer of a tris[tri(trimethylsiloxy)silylethyldimethylsiloxy]silylpropyl carbosiloxane dendrimer.

The monomers (A1) and (B1) correspond, respectively, to the particular monomers (A) and (B).

According to one embodiment, a vinyl polymer containing at least one carbosiloxane dendrimer-based unit may comprise a tris[tri(trimethylsiloxy)silylethyldimethylsiloxy]silylpropyl carbosiloxane dendrimer-based unit corresponding to one of the formulae:

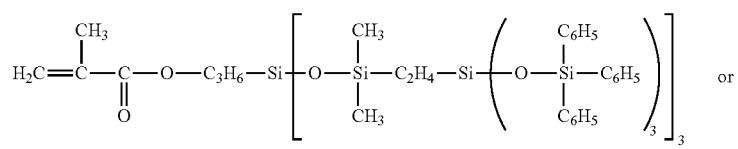

-continued

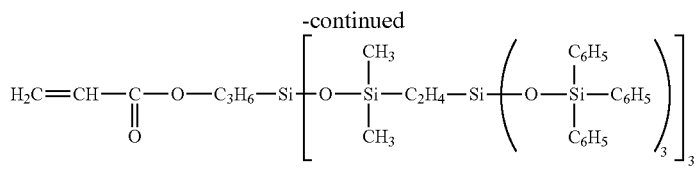

According to one preferred mode, a vinyl polymer containing at least one carbosiloxane dendrimer-based unit used in the invention comprises at least one butyl acrylate monomer.
According to one embodiment, a vinyl polymer may also comprise at least one fluoro organic group.

Structures in which the polymerized vinyl units constitute the backbone and carbosiloxane dendritic structures and also organofluorine groups are attached to side chains are particularly preferred.

The organofluorine groups may be obtained by replacing with fluorine atoms all or some of the hydrogen atoms of methyl, ethyl, propyl, isopropyl, butyl, isobutyl, tert-butyl, pentyl, neopentyl, hexyl, cyclohexyl, heptyl, octyl, nonyl, decyl, undecyl, dodecyl, tridecyl, tetradecyl, hexadecyl and octadecyl groups and other alkyl groups of 1 to 20 carbon atoms, and also alkyloxyalkylene groups of 6 to 22 carbon atoms.

The groups represented by the formula —(CH$_2$)$_x$—(CF$_2$)$_y$—R$^{13}$ are suggested as examples of fluoroalkyl groups obtained by substituting fluorine atoms for hydrogen atoms of alkyl groups. In the formula, the index "x" is 0, 1, 2 or 3 and "y" is an integer from 1 to 20. R$^{13}$ is an atom or a group chosen from a hydrogen atom, a fluorine atom, —CH(CF$_3$)$_2$— or CF(CF$_3$)$_2$. Such alkyl groups substituted with fluorine are illustrated by the linear or branched polyfluoroalkyl or perfluoroalkyl groups represented by the formulae presented below: —CF$_3$, —C$_2$F$_5$, -nC$_3$F$_7$, —CF(CF$_3$)$_2$, -nC$_4$F$_9$, CF$_2$CF(CF$_3$)$_2$, -nC$_5$F$_{11}$, -nC$_6$F$_{13}$, -nC$_5$F$_{17}$, —CH$_2$CF$_3$, —CH(CF$_3$)$_2$, CH$_2$CH(CF$_3$)$_2$—CH$_2$(CF$_2$)$_2$F, —CH$_2$(CF$_2$)$_3$F, —CH$_2$(CF$_2$)$_4$F, —CH$_2$(CF$_2$)$_6$F, —CH$_2$(CF$_2$)$_5$F, —CH$_2$CH$_2$CF$_3$, —CH$_2$CH$_2$(CF$_2$)$_2$F, —CH$_2$CH$_2$(CF$_2$)$_3$F, —CH$_2$CH$_2$(CF$_2$)$_4$F, —CH$_2$CH$_2$(CF$_2$)$_6$F, —CH$_2$CH$_2$(CF$_2$)$_5$F, —CH$_2$CH$_2$(CF$_2$)$_{10}$F, —CH$_2$CH$_2$(CF$_2$)$_{12}$F, —CH$_2$CH$_2$(CF$_2$)$_{14}$F, —CH$_2$CH$_2$(CF$_2$)$_{16}$F, —CH$_2$CH$_2$CH$_2$CF$_3$, —CH$_2$CH$_2$CH$_2$(CF$_2$)$_2$F, —CH$_2$CH$_2$CH$_2$(CF$_2$)$_2$H, —CH$_2$(CF$_2$)$_4$H, and —CH$_2$CH$_2$(CF$_2$)$_3$H.

The groups represented by —CH$_2$CH$_2$—(CF$_2$)$_m$—CFR$^{14}$—[OCF$_2$CF(CF$_3$)]$_n$—OC$_3$F$_7$ are suggested as fluoroalkyloxyfluoroalkylene groups obtained by substituting fluorine atoms for hydrogen atoms of alkyloxyalkylene groups. In the formula, the index "m" is 0 or 1, "n" is 0, 1, 2, 3, 4 or 5, and R$^{14}$ is a fluorine atom CF$_3$. Such fluoroalkyloxyfluoroalkylene groups are exemplified by the perfluoroalkyloxyfluoroalkylene groups represented by the formulae presented below: —CH$_2$CH$_2$CF(CF$_3$)—[OCF$_2$CF(CF$_3$)]$_n$—OC$_3$F$_7$, —CH$_2$CH$_2$CF$_2$CF$_2$—[OCF$_2$CF(CF$_3$)]$_n$—OC$_3$F$_7$.

The number-average molecular weight of the vinyl polymer used in the present invention may be between 3000 and 2 000 000 and more preferably between 5000 and 800 000.

This type of fluorinated vinyl polymer may be obtained by addition:
of a vinyl monomer (M2) without an organofluorine group,
onto a vinyl monomer (M1) containing organofluorine groups, and a carbosiloxane dendrimer (B) as defined above of general formula (I) as defined above,
by subjecting them to a copolymerization.

Thus, according to one embodiment, a composition of the invention may comprise a vinyl polymer bearing at least one carbosiloxane dendrimer-based unit derived from the copolymerization of a vinyl monomer (M1) as defined above, optionally a vinyl monomer (M2) as defined above, and a carbosiloxane dendrimer (B) as defined above,
the said vinyl polymer having a copolymerization ratio between the monomer (M1) and the monomer (M2) of from 0.1 to 100:99.9 to 0% by weight, and a copolymerization ratio between the sum of the monomers (M1) and (M2) and the monomer (B) of from 0.1 to 99.9:99.9 to 0.1% by weight.

The vinyl monomers (M1) containing organofluorine groups in the molecule are preferably monomers represented by the general formula:

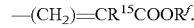

In this formula, R$^{15}$ is a hydrogen atom or a methyl group and R$^f$ is an organofluorine group exemplified by the fluoroalkyl and fluoroalkyloxyfluoroalkylene groups described above. The compounds represented by the formulae presented below are suggested as specific examples of the component (M1). In the formulae presented below "z" is an integer from 1 to 4.

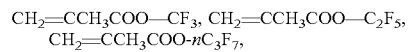

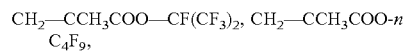

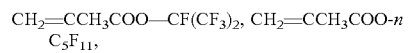

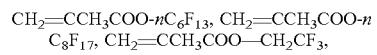

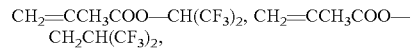

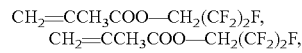

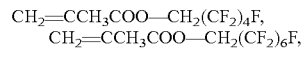

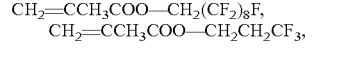

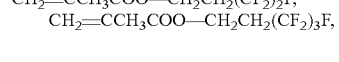

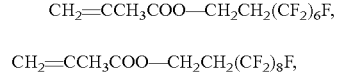

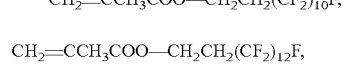

$CH_2=CCH_3COO-CH_2CH_2CH_2(CF_2)_2F$,
$CH_2=CCH_3COO-CH_2CH_2CH_2(CF_2)_2H$, $CH_2=CCH_3COO-CH_2(CF_2)_4H$,
$CH_2=CCH_3COO-(CF_2)_3H$, $CH_2=CCH_3COO-CH_2CH_2CF(CF_3)-[OCF_2-CF(CF_3)]_Z-OC_3F_7$, $CH_2=CCH_3COO-CH_2CH_2CF_2CF_2-[OCF_2-CF(CF_3)]_Z-OC_3F_7$, $CH_2=CHCOO-CF_3$, $CH_2=CHCOO-C_2F_5$, $CH_2=CHCOO-nC_3F_7$, $CH_2=CHCOO-CF(CF_3)_2$, $CH_2=CHCOO-nC_4F_8$, $CH_2=CHCOO-CF_2CF(CF_3)_2$, $CH_2=CHCOO-nC_5F_{11}$, $CH_2=CHCOO-nC_6F_{13}$, $CH_2=CHCOO-nC_8F_{17}$, $CH_2=CHCOO-CH_2CF_3$, $CH_2=CHCOO-CH(CF_3)_2$, $CH_2=CHCOO-CH_2CH(CF_3)_2$, $CH_2=CHCOO-CH_2(CF_2)_2F$, $CH_2=CHCOO-CH_2(CF_2)_3F$, $CH_2=CHCOO-CH_2(CF_2)_4F$, $CH_2=CHCOO-CH_2(CF_2)_6F$, $CH_2=CHCOO-CH_2(CF_2)_8F$, $CH_2=CHCOO-CH_2CH_2CF_3$, $CH_2=CHCOO-CH_2CH_2(CF_2)_2F$, $CH_2=CHCOO-CH_2CH_2(CF_2)_3F$, $CH_2=CHCOO-CH_2CH_2(CF_2)_4F$, $CH_2=CHCOO-CH_2CH_2(CF_2)_6F$, $CH_2=CHCOO-CH_2CH_2(CF_2)_8F$, $CH_2=HCOO-CH_2CH_2(CF_2)_{10}F$, $CH_2=CHCOO-CH_2CH_2-(CF_2)_{12}F$, $CH_2=CHCOO-CH_2CH_2(CF_2)_{14}F$, $CH_2=CHCOO-CH_2CH_2(CF_2)_{16}F$, $CH_2=CHCOO-CH_2CH_2CH_2CF_3$, $CH_2=CHCOO-CH_2CH_2CH_2(CF_2)_2F$, $CH_2=CHCOO-CH_2CH_2CH_2(CF_2)_2H$, $CH_2=CHCOO-CH_2(CF_2)_4H$, $CH_2=CHCOO-CH_2CH_2(CF_2)_3H$, $CH_2=CHCOO-CH_2CH_2CF(CF_3)-, [OCF_2-CF(CF_3)]_Z-OC_3F_7$, $CH_2=CHCOO-CH_2CH_2CF_2CF_2(CF_3)-[OCF_2-CF(CF_3)]_2-OC_3F_7$.

Among these, the vinyl polymers represented by the formulae presented below are preferable:

$CH_2=CHCOO-CH_2CH_2(CF_2)_6F$, $CH_2=CHCOO-CH_2CH_2(CF_2)_8F$, $CH_2=CCH_3COO-CH_2CH_2(CF_2)_6F$, $CH_2=CCH_3COO-CH_2CH_2(CF_2)_8F$, $CH_2=CHCOO-CH_2CF_3$, $CH_2=CCH_3COO-CH_2CF_3$.

The vinyl polymers represented by the formulae presented below are particularly preferable:

$CH_2=CHCOO-CH_2CF_3$, $CH_2=CCHCOO-CH_2CF_3$.

The vinyl monomers (M2) not containing any organofluorine groups in the molecule may be any monomer containing radical-polymerizable vinyl groups illustrated, for example, by methyl acrylate, methyl methacrylate, ethyl acrylate, ethyl methacrylate, n-propyl acrylate, n-propyl methacrylate, isopropyl acrylate, isopropyl methacrylate, and other lower alkyl acrylates or methacrylates; glycidyl acrylate, glycidyl methacrylate; n-butyl acrylate, n-butyl methacrylate, isobutyl acrylate, isobutyl methacrylate, tert-butyl acrylate, tert-butyl methacrylate, n-hexyl acrylate, n-hexyl methacrylate, n-hexyl acrylate, n-hexyl methacrylate, cyclohexyl acrylate, cyclohexyl methacrylate, 2-ethylhexyl acrylate, 2-ethylhexyl methacrylate, octyl acrylate, octyl methacrylate, lauryl acrylate, lauryl methacrylate, stearyl acrylate, stearyl methacrylate, and other higher acrylates and methacrylates; vinyl acetate, vinyl propionate and other lower fatty acid vinyl esters; vinyl butyrate, vinyl caproate, vinyl 2-ethylhexanoate, vinyl laurate, vinyl stearate, and other higher fatty acid esters; styrene, vinyltoluene, benzyl acrylate, benzyl methacrylate, phenoxyethyl acrylate, phenoxyethyl methacrylate, vinylpyrrolidone, and other vinylaromatic monomers; dimethylaminoethyl acrylate, dimethylaminoethyl methacrylate, diethylaminoethyl acrylate, diethylaminoethyl methacrylate, and other aminovinyl monomers, acrylamide, methacrylamide, N-methylolacrylamide, N-methylolmethacrylamide, N-methoxymethylacrylamide, N-methoxymethylmethacrylamide, isobutoxymethoxyacrylamide, isobutoxymethoxymethacrylamide, N,N-dimethylacrylamide, N,N-dimethylmethacrylamide, and other vinylamide monomers; hydroxyethyl acrylate, hydroxyethyl methacrylate, acrylic acid hydroxypropyl alcohol, methacrylic acid hydroxypropyl alcohol, and other hydroxyvinyl monomers; acrylic acid, methacrylic acid, itaconic acid, crotonic acid, fumaric acid, maleic acid, and other vinylcarboxylic acid monomers; tetrahydrofurfuryl acrylate, tetrahydrofurfuryl methacrylate, butoxyethyl acrylate, butoxyethyl methacrylate, ethoxydiethylene glycol acrylate, ethoxydiethylene glycol methacrylate, polyethylene glycol acrylate, polyethylene glycol methacrylate, polypropylene glycol monoacrylate, polypropylene glycol monomethacrylate, hydroxybutyl vinyl ether, cetyl vinyl ether, 2-ethylhexyl vinyl ether, and other vinyl monomers containing an ether bond; acryloxypropyltrimethoxysilane, methacryloxypropyltrimethoxysilane, polydimethylsiloxanes containing acryl or methacryl groups at one of the ends, polydimethylsiloxanes containing alkenylaryl groups at one of the ends and other silicone compounds containing unsaturated groups; butadiene; vinyl chloride; vinylidene chloride, acrylonitrile, methacrylonitrile; dibutyl fumarate; maleic anhydride; dodecylsuccinic anhydride; acryl glycidyl ether, methacryl glycidyl ether, 3,4-epoxycyclohexylmethyl acrylate, 3,4-epoxycyclohexylmethyl methacrylate, alkali metal salts, ammonium salts and organic amine salts of acrylic acid, of methacrylic acid, of itaconic acid, of crotonic acid, of fumaric acid, of maleic acid and of other radical-polymerizable unsaturated carboxylic acids, radical-polymerizable unsaturated monomers containing sulfonic acid groups, such as styrene sulfonic acid and also the alkali metal salts thereof, the ammonium salts thereof and the organic amine salts thereof; the quaternary ammonium salts derived from acrylic acid or methacrylic acid, such as 2-hydroxy-3-methacryloxypropyltrimethylammonium chloride, methacrylic acid esters of a tertiary amine alcohol, such as the diethylamine ester of methacrylic acid and quaternary ammonium salts thereof.

In addition, it is also possible to use as vinyl monomers (M2) the polyfunctional vinyl monomers illustrated, for example, by trimethylolpropane triacrylate, trimethylolpropane trimethacrylate, pentaerythrityl triacrylate, pentaerythrityl trimethacrylate, ethylene glycol diacrylate, ethylene glycol dimethacrylate, tetraethylene glycol diacrylate, tetraethylene glycol dimethacrylate, polyethylene glycol diacrylate, polyethylene glycol dimethacrylate, 1,4-butanediol diacrylate, 1,4-butanediol dimethacrylate, 1,6-hexanediol diacrylate, 1,6-hexanediol dimethacrylate, neopentyl glycol diacrylate, neopentyl glycol dimethacrylate, trimethylolpropanetrioxyethyl acrylate, trimethylolpropanetrioxyethyl methacrylate, tris(2-hydroxyethyl)isocyanurate diacrylate, tris(2-hydroxyethyl)isocyanurate dimethacrylate, tris(2-hydroxyethyl)isocyanurate triacrylate, tris(2-hydroxyethyl)isocyanurate trimethacrylate, polydimethylsiloxane in which the two ends of the molecular chain are blocked with alkenylaryl groups, and other silicone compounds containing unsaturated groups.

As regards the ratio mentioned above in which (M1) and (M2) are copolymerized, the weight ratio between (M1) and (M2) is preferably in the range 1:99 to 100:0.

Y may be chosen, for example, from organic groups bearing acrylic or methacrylic groups, organic groups bearing alkenylaryl groups, or alkenyl groups of 2 to 10 carbon atoms.

The organic groups bearing acrylic or methacrylic groups and the alkenylaryl groups are as defined above.

Among the compounds (B), mention may be made, for example, of the following compounds:

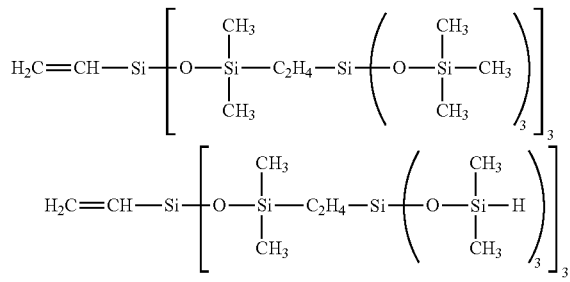

The carbosiloxane dendrimers (B) may be prepared using the process for preparing siloxane/silylalkylene branched copolymers described in document EP 1 055 674.

For example, they may be prepared by subjecting organic alkenyl silicones and silicone compounds comprising hydrogen atoms linked to silicon, represented by formula (IV) as defined above, to a hydrosilylation reaction.

The copolymerization ratio (by weight) between the monomer (B) and the monomers (M1) and (M2) is preferably in the range from 1:99 to 99:1 and even more preferably in the range from 5:95 to 95:1.

Amino groups may be introduced into the side chains of the vinyl polymer using, included in the component (M2), vinyl monomers containing amino groups, such as dimethylaminoethyl acrylate, dimethylaminoethyl methacrylate, diethylaminoethyl acrylate and diethylaminoethyl methacrylate, followed by performing a modification with potassium acetate monochloride, ammonium acetate monochloride, the aminomethylpropanol salt of monochloroacetic acid, the triethanolamine salt of monobromoacetic acid, sodium monochloropropionate, and other alkali metal salts of halogenated fatty acids; otherwise, carboxylic acid groups may be introduced into the side chains of the vinyl polymer using, included in the component (M2), vinyl monomers containing carboxylic acids, such as acrylic acid, methacrylic acid, itaconic acid, crotonic acid, fumaric acid and maleic acid, and the like, followed by neutralizing the product with triethylamine, diethylamine, triethanolamine and other amines.

A fluoro vinyl polymer may be one of the polymers described in the examples of patent application WO 03/045 337.

According to one preferred embodiment, a vinyl polymer grafted in the sense of the present invention may be conveyed in an oil or a mixture of oils, which are preferably volatile, chosen in particular from silicone oils and hydrocarbon-based oils, and mixtures thereof.

According to one particular embodiment, a silicone oil that is suitable for use in the invention may be cyclopentasiloxane.

According to another particular embodiment, a hydrocarbon-based oil that is suitable for use in the invention may be isododecane.

Vinyl polymers grafted with at least one carbosiloxane dendrimer-based unit that may be particularly suitable for use in the present invention are the polymers sold under the names TIB 4-100, TIB 4-101, TIB 4-120, TIB 4-130, TIB 4-200, FA 4002 ID (TIB 4-202), TIB 4-220 and FA 4001 CM (TIB 4-230) by the company Dow Corning.

According to one embodiment, the composition according to the invention comprises the vinyl polymer bearing at least one carbosiloxane dendrimer-based unit in an active material content of from 0.5% to 20%, in particular from 1% to 15%, more particularly from 2% to 10% and preferably from 3% to 5% by weight relative to the total weight of the said composition.

Perlite

The compositions of the invention comprise at least perlite.

Perlite is a natural glass (sodium potassium aluminium silicate) of volcanic origin, resulting from the rapid cooling of lava, and is in the form of small particles resembling pearls. When it is heated beyond 800° C., it has the particularity of losing the water it contains and of taking a porous expanded form (representing from four to twenty times its initial volume), enabling it to absorb large amounts of oil.

The perlite particles used according to the invention have a small particle size.

In the context of the present invention, the term "particle size" denotes the mean diameter of the said particles.

Thus, the perlite particles may preferably have a particle size distribution such that at least 50% of the particles are smaller than 25 µm in size.

Preferably, the perlite particles according to the invention have a particle size distribution such that at least 50% of the particles are smaller than 20 µm in size.

In addition, they preferentially have a particle size distribution such that 90% by weight are less than 55 µm and preferably less than 40 µm in size. It is moreover preferable for 90% by weight of the particles to be larger than 5 µm in size.

The amount of perlites particles used according to the invention may advantageously represent from 0.001% to 15% by weight relative to the total weight of the composition, preferably from 0.05% to 10% by weight, more preferentially from 0.1% to 5% and more preferentially from 0.15% to 3% by weight relative to the total weight of the composition.

The perlite particles that may be used according to the invention are especially commercially available from the company World Minerals under the trade names Optimat 2550 OR and Optimat 1430 OR.

Physiologically Acceptable Medium

Besides the compounds indicated previously, a composition according to the invention comprises a physiologically acceptable medium.

The term "physiologically acceptable medium" is intended to denote a medium that is particularly suitable for applying a composition according to the invention to the skin.

The physiologically acceptable medium is generally adapted to the nature of the support onto which the composition is to be applied, and also to the form in which the composition is to be packaged.

A composition of the invention may be a dispersion or an emulsion.

A dispersion may be made as an aqueous phase or as an oily phase.

An emulsion may have an oily or aqueous continuous phase. Such an emulsion may be, for example, an inverse (W/O) emulsion or a direct (O/W) emulsion, or alternatively a multiple emulsion (W/O/W or O/W/O).

In the case of emulsions, inverse (W/O) emulsions are preferred.

Aqueous Phase

The composition according to the invention may comprise an aqueous phase.

The aqueous phase comprises water. A water that is suitable for use in the invention may be a floral water such as cornflower water and/or a mineral water such as Vittel water, Lucas water or La Roche Posay water and/or a spring water.

The aqueous phase may also comprise water-miscible organic solvents (at room temperature: 25° C.), for instance monoalcohols containing from 2 to 6 carbon atoms, such as ethanol or isopropanol; polyols especially containing from 2 to 20 carbon atoms, preferably containing from 2 to 10 carbon atoms and preferentially containing from 2 to 6 carbon atoms, such as glycerol, propylene glycol, butylene glycol, pentylene glycol, hexylene glycol, dipropylene glycol or diethylene glycol; glycol ethers (especially containing from 3 to 16 carbon atoms) such as mono-, di- or tripropylene glycol ($C_1$-$C_4$)alkyl ethers, mono-, di- or triethylene glycol ($C_1$-$C_4$)alkyl ethers, and mixtures thereof.

The aqueous phase may also comprise stabilizers, for example sodium chloride, magnesium dichloride or magnesium sulfate.

The aqueous phase may also comprise any water-soluble or water-dispersible compound that is compatible with an aqueous phase, such as gelling agents, film-forming polymers, thickeners or surfactants, and mixtures thereof.

In particular, a composition of the invention may comprise an aqueous phase in a content ranging from 1% to 80% by weight, especially from 5% to 50% and more particularly from 10% to 45% by weight relative to the total weight of the composition.

According to another embodiment, a composition of the invention may be anhydrous.

An anhydrous composition may comprise less than 5% by weight of water relative to the total weight of the composition, in particular less than 3%, especially less than 2% and more particularly less than 1% by weight of water relative to the total weight of the composition.

More particularly, an anhydrous composition may be free of water.

Fatty Phase

A cosmetic composition in accordance with the present invention may comprise at least one liquid and/or solid fatty phase.

According to one embodiment of the present invention, the perlite and the vinyl polymer bearing at least one carbosiloxane dendrimer-based unit are present in the fatty phase.

According to one embodiment, the composition according to the present invention is in the form of an emulsion.

The perlite and the vinyl polymer bearing at least one carbosiloxane dendrimer-based unit are generally present in the fatty phase of the said emulsion.

In particular, a composition of the invention may comprise at least one liquid fatty phase, especially at least one oil as mentioned below.

The term "oil" means any fatty substance that is in liquid form at room temperature (20-25° C.) and at atmospheric pressure.

A composition of the invention may comprise a liquid fatty phase in a content ranging from 1% to 90%, in particular from 5% to 80%, in particular from 10% to 70% and more particularly from 20% to 50% by weight relative to the total weight of the composition.

The oily phase that is suitable for preparing the cosmetic compositions according to the invention may comprise hydrocarbon-based oils, silicone oils, fluoro oils or non-fluoro oils, or mixtures thereof.

The oils may be volatile or non-volatile.

They may be of animal, plant, mineral or synthetic origin.

The term "non-volatile oil" means an oil that remains on the skin or the keratin fibre at room temperature and atmospheric pressure. More specifically, a non-volatile oil has an evaporation rate strictly less than 0.01 mg/cm$^2$/min.

To measure this evaporation rate, 15 g of oil or of oil mixture to be tested are placed in a crystallizing dish 7 cm in diameter, which is placed on a balance in a large chamber of about 0.3 m$^3$ that is temperature-regulated, at a temperature of 25° C., and hygrometry-regulated, at a relative humidity of 50%. The liquid is allowed to evaporate freely, without stirring it, while providing ventilation by means of a fan (Papst-Motoren, reference 8550 N, rotating at 2700 rpm) placed in a vertical position above the crystallizing dish containing said oil or said mixture, the blades being directed towards the crystallizing dish, 20 cm away from the bottom of the crystallizing dish. The mass of oil remaining in the crystallizing dish is measured at regular intervals. The evaporation rates are expressed in mg of oil evaporated per unit of area (cm$^2$) and per unit of time (minutes).

The term "volatile oil" means any non-aqueous medium that is capable of evaporating on contact with the skin or the lips in less than one hour, at room temperature and atmospheric pressure. The volatile oil is a cosmetic volatile oil, which is liquid at room temperature. More specifically, a volatile oil has an evaporation rate of between 0.01 and 200 mg/cm$^2$/min, limits included.

For the purposes of the present invention, the term "silicone oil" means an oil comprising at least one silicon atom, and especially at least one Si—O group.

The term "fluoro oil" means an oil comprising at least one fluorine atom.

The term "hydrocarbon-based oil" means an oil mainly containing hydrogen and carbon atoms.

The oils may optionally comprise oxygen, nitrogen, sulfur and/or phosphorus atoms, for example in the form of hydroxyl or acid radicals.

Volatile Oils

The volatile oils may be chosen from hydrocarbon-based oils containing from 8 to 16 carbon atoms, and especially $C_8$-$C_{16}$ branched alkanes (also known as isoparaffins), for instance isododecane (also known as 2,2,4,4,6-pentamethylheptane), isodecane and isohexadecane, for instance the oils sold under the trade names Isopar® or Permethyl®.

Volatile oils that may also be used include volatile silicones, for instance volatile linear or cyclic silicone oils, especially those with a viscosity of less than or equal to 8 centistokes (cSt) ($8 \times 10^{-6}$ m$^2$/s), and especially containing from 2 to 10 silicon atoms and in particular from 2 to 7 silicon atoms, these silicones optionally comprising alkyl or alkoxy groups containing from 1 to 10 carbon atoms. As volatile silicone oils that may be used in the invention, mention may be made especially of dimethicones with viscosities of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Volatile fluoro oils such as nonafluoromethoxybutane or perfluoromethyl-cyclopentane, and mixtures thereof, may also be used.

According to one embodiment, a composition of the invention may comprise from 1% to 80% by weight, or even from 5% to 70% by weight, or even from 10% to 60% by weight and especially from 15% to 50% by weight of volatile oil relative to the total weight of the composition.

Non-Volatile Oils

The non-volatile oils may be chosen especially from non-volatile hydrocarbon-based, fluoro and/or silicone oils.

Non-volatile hydrocarbon-based oils that may especially be mentioned include:
- hydrocarbon-based oils of animal origin, such as perhydrosqualene, hydrocarbon-based oils of plant origin, such as phytostearyl esters, such as phytostearyl oleate, phytostearyl isostearate and lauroyl/octyldodecyl/phytostearyl glutamate (Ajinomoto, Eldew PS203), triglycerides formed from fatty acid esters of glycerol, in particular in which the fatty acids may have chain lengths ranging from $C_4$ to $C_{36}$ and especially from $C_{18}$ to $C_{36}$, these oils possibly being linear or branched, and saturated or unsaturated; these oils may especially be heptanoic or octanoic triglycerides, shea oil, alfalfa oil, poppy oil, winter squash oil, millet oil, barley oil, quinoa oil, rye oil, candlenut oil, passionflower oil, shea butter, aloe vera oil, sweet almond oil, peach stone oil, groundnut oil, argan oil, avocado oil, baobab oil, borage oil, broccoli oil, calendula oil, camelina oil, canola oil, carrot oil, safflower oil, flax oil, rapeseed oil, cotton oil, coconut oil, marrow seed oil, wheatgerm oil, jojoba oil, lily oil, macadamia oil, corn oil, meadowfoam oil, St John's Wort oil, monoi oil, hazelnut oil, apricot kernel oil, walnut oil, olive oil, evening primrose oil, palm oil, blackcurrant pip oil, kiwi seed oil, grapeseed oil, pistachio oil, winter squash oil, pumpkin oil, musk rose oil, sesame oil, soybean oil, sunflower oil, castor oil and watermelon seed oil, and mixtures thereof, or alternatively caprylic/capric acid triglycerides, such as those sold by the company Stearineries Dubois or those sold under the names Miglyol 810®, 812® and 818® by the company Dynamit Nobel,
- linear or branched hydrocarbons of mineral or synthetic origin, such as liquid paraffins and derivatives thereof, petroleum jelly, polydecenes, polybutenes, hydrogenated polyisobutene such as Parleam, and squalane;
- synthetic ethers containing from 10 to 40 carbon atoms;
- synthetic esters, for instance the oils of formula $R_1COOR_2$, in which $R_1$ represents a linear or branched fatty acid residue containing from 1 to 40 carbon atoms and $R_2$ represents a hydrocarbon-based chain, which is especially branched, containing from 1 to 40 carbon atoms, on condition that the sum of the number of carbon atoms in the chains $R_1$ and $R_2$ is greater than or equal to 10. The esters may be chosen especially from fatty acid esters of alcohols, for instance cetostearyl octanoate, isopropyl alcohol esters, such as isopropyl myristate, isopropyl palmitate, ethyl palmitate, 2-ethylhexyl palmitate, isopropyl stearate, isopropyl isostearate, isostearyl isostearate, octyl stearate, hydroxylated esters, for instance isostearyl lactate, octyl hydroxystearate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate, 2-ethylhexyl palmitate, alkyl benzoates, polyethylene glycol diheptanoate, propylene glycol 2-diethylhexanoate, and mixtures thereof, $C_{12}$-$C_{15}$ alcohol benzoates, hexyl laurate, neopentanoic acid esters, for instance isodecyl neopentanoate, isotridecyl neopentanoate, isostearyl neopentanoate, octyldodecyl neopentanoate, isononanoic acid esters, for instance isononyl isononanoate, isotridecyl isononanoate, octyl isononanoate, hydroxylated esters, for instance isostearyl lactate and diisostearyl malate,
- polyol esters and pentaerythritol esters, for instance dipentaerythrityl tetrahydroxystearate/tetraisostearate,
- esters of diol dimers and of diacid dimers, such as Lusplan DD-DA5® and Lusplan DD-DA7® sold by the company Nippon Fine Chemical and described in patent application US 2004-175 338,
- copolymers of a diol dimer and of a diacid dimer and esters thereof, such as dilinoleyl diol dimer/dilinoleic dimer copolymers and esters thereof, for instance Plandool-G,
- copolymers of polyols and of diacid dimers, and esters thereof, such as Hailuscent ISDA or the dilinoleic acid/butanediol copolymer,
- fatty alcohols that are liquid at room temperature, with a branched and/or unsaturated carbon-based chain containing from 12 to 26 carbon atoms, for instance 2-octyldodecanol, isostearyl alcohol, oleyl alcohol, 2-hexyldecanol, 2-butyloctanol and 2-undecyl-pentadecanol;
- $C_{12}$-$C_{22}$ higher fatty acids, such as oleic acid, linoleic acid or linolenic acid, and mixtures thereof,
- dialkyl carbonates, the two alkyl chains possibly being identical or different, such as dicaprylyl carbonate sold under the name Cetiol CC® by Cognis,
- oils of high molar mass, in particular having a molar mass ranging from about 400 to about 10 000 g/mol, in particular from about 650 to about 10 000 g/mol, in particular from about 750 to about 7500 g/mol and more particularly ranging from about 1000 to about 5000 g/mol. As oils of high molar mass that may be used in the present invention, mention may especially be made of oils chosen from:
  lipophilic polymers,
  linear fatty acid esters with a total carbon number ranging from 35 to 70,
  hydroxylated esters,
  aromatic esters,
  $C_{24}$-$C_{28}$ branched fatty acid or fatty alcohol esters,
  silicone oils,
  oils of plant origin,
  and mixtures thereof;

optionally partially hydrocarbon-based and/or silicone fluoro oils, for instance fluorosilicone oils, fluoropolyethers and fluorosilicones as described in document EP-A-847 752;

silicone oils, for instance linear or cyclic non-volatile polydimethylsiloxanes (PDMS); polydimethylsiloxanes comprising alkyl, alkoxy or phenyl groups, which are pendant or at the end of a silicone chain, these groups containing from 2 to 24 carbon atoms; phenyl silicones, for instance phenyl trimethicones, phenyl dimethicones, phenyl trimethylsiloxy diphenyl siloxanes, diphenyl dimethicones, diphenyl methyldiphenyl trisiloxanes and 2-phenylethyl trimethylsiloxy silicates, and mixtures thereof.

According to one particular embodiment, the fatty phase of the composition according to the invention can contain only volatile compounds.

Lipophilic Structuring Agent

A composition according to the invention may comprise at least one structuring agent for the liquid fatty phase, chosen from a wax and a pasty compound, and mixtures thereof.

In particular, a wax that is suitable for use in the invention may be chosen especially from waxes of animal, plant, mineral or synthetic origin, and mixtures thereof.

As examples of waxes that may be used according to the invention, mention may be made of:

waxes of animal origin such as beeswax, spermaceti, lanolin wax and lanolin derivatives, plant waxes such as carnauba wax, candelilla wax, ouricurry wax, Japan wax, cocoa butter, cork fibre wax or sugarcane wax, mineral waxes, for example paraffin wax, petroleum jelly wax, lignite wax or microcrystalline waxes, or ozokerites, synthetic waxes, including polyethylene wax and the waxes obtained by Fisher-Tropsch synthesis, silicone waxes, in particular substituted linear polysiloxanes; examples that may be mentioned include polyether silicone waxes, alkyl or alkoxy dimethicones containing from 16 to 45 carbon atoms, and alkyl methicones, for instance the $C_{30}$-$C_{45}$ alkyl methicone sold under the trade name AMS C 30 by Dow Corning, hydrogenated oils that are concrete at 25° C., such as hydrogenated castor oil, hydrogenated jojoba oil, hydrogenated palm oil, hydrogenated tallow, hydrogenated coconut oil and fatty esters that are solid at 25° C., for instance the $C_{20}$-$C_{40}$ alkyl stearate sold under the trade name Kester Wax K82H by the company Koster Keunen, and mixtures thereof.

Preferably, use will be made of polyethylene waxes, microcrystalline waxes, carnauba waxes, hydrogenated jojoba oil, candelilla waxes and beeswaxes, and/or mixtures thereof.

A composition according to the invention may also comprise at least one pasty compound.

The presence of a pasty compound may make it possible advantageously to impart improved comfort during the application of a composition of the invention to keratin fibres.

Such a compound may be chosen advantageously from lanolin and derivatives thereof; polymeric or non-polymeric silicone compounds; polymeric or non-polymeric fluoro compounds; vinyl polymers, especially olefin homopolymers; olefin copolymers; hydrogenated diene homopolymers and copolymers; linear or branched oligomers, homopolymers or copolymers of alkyl(meth)acrylates preferably containing a $C_5$-$C_{30}$ alkyl group; oligomers, homopolymers and copolymers of vinyl esters containing $C_8$-$C_{30}$ alkyl groups; oligomers, homopolymers and copolymers of vinyl ethers containing $C_8$-$C_{30}$ alkyl groups; liposoluble polyethers resulting from the polyetherification between one or more $C_2$-$C_{100}$ and in particular $C_2$-$C_{50}$ diols; esters of a fatty acid or a fatty alcohol; and mixtures thereof.

Among the esters, mention may be made especially of:

esters of a glycerol oligomer, especially diglycerol esters, for instance poly(2-glyceryl triisostearate), condensates of adipic acid and of glycerol, for which some of the hydroxyl groups of the glycerols have reacted with a mixture of fatty acids, such as stearic acid, capric acid, stearic acid and isostearic acid and 12-hydroxystearic acid, especially such as those sold under the brand name Softisan 649 by the company Sasol or such as poly[bis(diglyceryl 2-acyladipate)]; arachidyl propionate sold under the brand name Waxenol 801 by Alzo; phytosterol esters; fatty acid triglycerides and derivatives thereof, such as hydrogenated cocoyl glycerides; non-crosslinked polyesters resulting from polycondensation between a linear or branched $C_4$-$C_{50}$ dicarboxylic or polycarboxylic acid and a $C_2$-$C_{50}$ diol or polyol; aliphatic esters resulting from the esterification of an aliphatic hydroxycarboxylic acid ester with an aliphatic carboxylic acid; polyesters resulting from the esterification, with a polycarboxylic acid, of an aliphatic hydroxycarboxylic acid, the said ester comprising at least two hydroxyl groups, such as the products Risocast DA-H® and Risocast DA-L®; and mixtures thereof.

The structuring agent(s) may be present in a composition of the invention in a content ranging from 0.1% to 30% by weight and preferably from 0.5% to 20% by weight relative to the total weight of the composition.

Thickeners

Depending on the fluidity of the composition that it is desired to obtain, it is possible to incorporate one or more thickeners or gelling agents into a composition of the invention.

A thickener or gelling agent that is suitable for use in the invention may be hydrophilic, i.e. soluble or dispersible in water.

Hydrophilic gelling agents that may be mentioned in particular include water-soluble or water-dispersible thickening polymers. These polymers may be chosen especially from: modified or unmodified carboxyvinyl polymers, such as the products sold under the name Carbopol (CTFA name: Carbomer) by the company Goodrich; polyacrylates and polymethacrylates such as the products sold under the names Lubrajel and Norgel by the company Guardian or under the name Hispagel by the company Hispano Chimica; polyacrylamides; optionally crosslinked and/or neutralized 2-acrylamido-2-methylpropanesulfonic acid polymers and copolymers, for instance the poly(2-acrylamido-2-methylpropanesulfonic acid) sold by the company Clariant under the name Hostacerin AMPS (CTFA name: ammonium polyacryldimethyltauramide); crosslinked anionic copolymers of acrylamide and of AMPS, which are in the form of a W/O emulsion, such as those sold under the name Sepigel 305 (CTFA name: Polyacrylamide/C13-14 isoparaffin/Laureth-7) and under the name Simulgel 600 (CTFA name: Acrylamide/Sodium acryloyldimethyltaurate copolymer/Isohexadecane/Polysorbate 80) by the company SEPPIC; polysaccharide biopolymers, for instance xanthan gum, guar gum, carob gum, acacia gum, scleroglucans, chitin and chitosan derivatives, carrageenans, gellans, alginates, celluloses such as microcrystalline cellulose, carboxymethyl cellulose, hydroxymethyl cellulose and hydroxypropyl cellulose; and mixtures thereof.

A thickener or gelling agent that is suitable for use in the invention may be lipophilic. It may be mineral or organic.

Examples of lipophilic thickeners that may be mentioned include modified clays such as modified magnesium silicate (Bentone gel VS38 from Rheox), modified hectorites such as hectorite modified with a $C_{10}$ to $C_{22}$ fatty acid ammonium chloride, for instance hectorite modified with distearyldimethylammonium chloride, for instance the product sold under the name Bentone 38V® by the company Elementis or the product sold under the name Bentone 38 CE by the company Rheox, or the product sold under the name Bentone Gel V5 5V by the company Elementis.

The polymeric organic lipophilic gelling agents are, for example, partially or completely crosslinked elastomeric organopolysiloxanes of three-dimensional structure, for instance those sold under the names KSG6®, KSG16® and KSG18® by Shin-Etsu, Trefil E-505C® and Trefil E-506C® by Dow Corning, Gransil SR-CYC®, SR DMF10®, SR-DC556®, SR 5CYC gel®, SR DMF 10 gel® and SR DC 556 gel® by Grant Industries and SF 1204® and JK 113® by General Electric; ethyl cellulose, for instance the product sold under the name Ethocel® by Dow Chemical; polycondensates of polyamide type resulting from the condensation between a dicarboxylic acid containing at least 32 carbon atoms, such as fatty acid dimers, and an alkylenediamine and in particular ethylenediamine, in which the polymer comprises at least one carboxylic acid end group esterified or amidated with at least one saturated and linear monoalcohol or monoamine containing from 12 to 30 carbon atoms, and in particular ethylenediamine/stearyl dilinoleate copolymers such as the product sold under the name Uniclear 100 VG® by Arizona Chemical; galactomannans comprising from one to six and in particular from two to four hydroxyl groups per saccharide, substituted with a saturated or unsaturated alkyl chain, for instance guar gum alkylated with $C_1$ to $C_6$, and in particular $C_1$ to $C_3$, alkyl chains, and mixtures thereof. Block copolymers of "diblock", "triblock" or "radial" type, of the polystyrene/polyisoprene or polystyrene/polybutadiene type, such as the products sold under the name Luvitol HSB® by the company BASF, of the polystyrene/copoly(ethylene-propylene) type, such as the products sold under the name Kraton® by the company Shell Chemical Co., or of the polystyrene/copoly(ethylene-butylene) type, and mixtures of triblock and radial (star) copolymers in isododecane, such as those sold by the company Penreco under the name Versagel®, for instance the mixture of butylene/ethylene/styrene triblock copolymer and of ethylene/propylene/styrene star copolymer in isododecane (Versagel M 5960).

Among the lipophilic gelling agents that may be used in a cosmetic composition of the invention, mention may also be made of fatty acid esters of dextrin, such as dextrin palmitates, especially such as those sold under the names Rheopearl IL® or Rheopearl KL® by the company Chiba Flour, hydrogenated plant oils, such as hydrogenated castor oil, fatty alcohols, in particular of $C_8$ to $C_{26}$ and more particularly $C_{12}$ to $C_{22}$, for instance myristyl alcohol, cetyl alcohol, stearyl alcohol or behenyl alcohol.

According to one embodiment, a composition of the invention may comprise thickeners in an active material content of from 0.01% to 40% by weight, especially from 0.1% to 20% by weight and in particular from 0.3% to 15% by weight relative to the total weight of the composition.

Dyestuffs

A composition according to the invention may also comprise at least one dyestuff.

A cosmetic composition in accordance with the invention may advantageously incorporate at least one dyestuff chosen from organic or mineral dyes, especially such as the pigments or nacres conventionally used in cosmetic compositions, liposoluble or water-soluble dyes, materials with a specific optical effect, and mixtures thereof.

The term "pigments" should be understood to mean white or coloured, inorganic or organic particles which are insoluble in an aqueous solution and are intended for colouring and/or opacifying the resulting film.

The pigments may be present in a proportion of from 0.1% to 40% by weight, especially from 1% to 30% by weight and in particular from 5% to 15% by weight relative to the total weight of the composition.

As inorganic pigments that can be used in the invention, mention may be made of titanium oxides, zirconium oxides or cerium oxides, and also zinc oxides, iron oxides or chromium oxides, ferric blue, manganese violet, ultramarine blue and chromium hydrate. According to one particular mode of the invention, the mineral pigments will be chosen from iron oxides and titanium oxides, and mixtures thereof.

It may also be a pigment having a structure that may be, for example, of sericite/brown iron oxide/titanium dioxide/silica type. Such a pigment is sold, for example, under the reference Coverleaf NS or JS by the company Chemicals and Catalysts, and has a contrast ratio in the region of 30.

The colorant may also comprise a pigment having a structure which may be, for example, of the type such as silica microspheres containing iron oxide. An example of a pigment having this structure is the product sold by the company Miyoshi under the reference PC Ball PC-LL-100 P, this pigment being constituted of silica microspheres containing yellow iron oxide.

Among the organic pigments that may be used in the invention, mention may be made of carbon black, pigments of D&C type, lakes based on cochineal carmine or on barium, strontium, calcium or aluminium, or alternatively the diketopyrrolopyrroles (DPP) described in documents EP 0 542 669, EP 0 787 730, EP 0 787 731 and WO 96/08537.

The term "nacres" should be understood as meaning iridescent or non-iridescent coloured particles of any form, especially produced by certain molluscs in their shell or alternatively synthesized, which have a colour effect via optical interference.

The nacres may be chosen from nacreous pigments such as titanium mica coated with an iron oxide, titanium mica coated with bismuth oxychloride, titanium mica coated with chromium oxide, titanium mica coated with an organic dye and also nacreous pigments based on bismuth oxychloride. They may also be mica particles at the surface of which are superposed at least two successive layers of metal oxides and/or of organic dyestuffs.

Examples of nacres that may also be mentioned include natural mica coated with titanium oxide, with iron oxide, with natural pigment or with bismuth oxychloride. Among the nacres available on the market, mention may be made of the nacres Timica, Flamenco and Duochrome (based on mica) sold by the company Engelhard, the Timiron nacres sold by the company Merck, the Prestige mica-based nacres, sold by the company Eckart, and the Sunshine synthetic mica-based nacres, sold by the company Sun Chemical.

The nacres may more particularly have a yellow, pink, red, bronze, orange, brown, gold and/or coppery colour or tint.

As illustrations of nacres that may be used in the context of the present invention, mention may be made of gold-coloured nacres sold especially by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the names Bronze fine (17384) (Colorona) and Bronze (17353) (Colorona) and by the company Engelhard under the name Super bronze (Cloisonne); the orange nacres sold especially by the company Engelhard under the names Orange 363C (Cloisonne) and Orange MCR 101 (Cosmica) and by the company Merck under the names Passion orange (Colorona) and Matte orange (17449) (Microna); the brown-tinted nacres sold especially by the company Engelhard under the names Nuantique copper 340XB (Cloisonne) and Brown CL4509 (Chromalite); the nacres with a copper tint sold especially by the company Engelhard under the name Copper 340A (Timica); the nacres with a red tint sold especially by the company Merck under the name Sienna fine (17386) (Colorona); the nacres with a yellow tint sold especially by the company Engelhard under the name Yellow (4502) (Chromalite); the red-tinted nacres with a golden tint sold especially by the company Engelhard under the name Sunstone G012 (Gemtone); the pink nacres sold especially by the company Engelhard under the name Tan opale G005 (Gemtone); the black nacres with a golden tint sold especially by the company Engelhard under the name Nu antique bronze 240 AB (Timica); the blue nacres sold especially by the company Merck under the name Matte blue (17433) (Microna); the white nacres with a silvery tint sold especially by the company Merck under the name Xirona Silver; and the golden-green pinkish-orange nacres sold especially by the company Merck under the name Indian summer (Xirona), and mixtures thereof.

The cosmetic composition according to the invention may also comprise water-soluble or fat-soluble dyes. The liposoluble dyes are, for example, Sudan red, DC Red 17, DC Green 6, β-carotene, soybean oil, Sudan brown, DC Yellow 11, DC Violet 2, DC Orange 5 and quinoline yellow. The water-soluble dyes are, for example, beetroot juice and caramel.

The cosmetic composition according to the invention may also contain at least one material with a specific optical effect.

This effect is different from a simple conventional hue effect, i.e. a unified and stabilized effect as produced by standard dyestuffs, for instance monochromatic pigments. For the purposes of the invention, the term "stabilized" means lacking an effect of variability of the colour as a function of the angle of observation or alternatively in response to a temperature change.

For example, this material may be chosen from particles with a metallic tint, goniochromatic colouring agents, diffracting pigments, thermochromic agents, optical brighteners, and also fibres, especially interference fibres. Needless to say, these various materials may be combined so as to afford the simultaneous manifestation of two effects, or even of a novel effect in accordance with the invention.

The particles with a metallic tint that may be used in the invention are chosen in particular from:
particles of at least one metal and/or of at least one metal derivative,
particles comprising a single-material or multi-material organic or inorganic substrate, at least partially coated with at least one layer with a metallic glint comprising at least one metal and/or at least one metal derivative, and
mixtures of said particles.

Among the metals that may be present in said particles, mention may be made, for example, of Ag, Au, Cu, Al, Ni, Sn, Mg, Cr, Mo, Ti, Zr, Pt, Va, Rb, W, Zn, Ge, Te and Se, and mixtures or alloys thereof. Ag, Au, Cu, Al, Zn, Ni, Mo and Cr and mixtures or alloys thereof (for example bronzes and brasses) are preferred metals.

The term "metal derivatives" is intended to denote compounds derived from metals, especially oxides, fluorides, chlorides and sulfides.

Illustrations of these particles that may be mentioned include aluminium particles, such as those sold under the names Starbrite 1200 EAC® by the company Siberline and Metalure® by the company Eckart.

Mention may also be made of metal powders of copper or of alloy mixtures such as the references 2844 sold by the company Radium Bronze, metallic pigments, for instance aluminium or bronze, such as those sold under the names Rotosafe 700 from the company Eckart, silica-coated aluminium particles sold under the name Visionaire Bright Silver from the company Eckart, and metal alloy particles, for instance the silica-coated bronze (alloy of copper and zinc) powders sold under the name Visionaire Bright Natural Gold from the company Eckart.

They may also be particles comprising a glass substrate, for instance those sold by the company Nippon Sheet Glass under the name Microglass Metashine.

The goniochromatic colouring agent may be chosen, for example, from multilayer interference structures and liquid-crystal colouring agents.

Examples of symmetrical multilayer interference structures that may be used in the compositions prepared in accordance with the invention are, for example, the following structures: $Al/SiO_2/Al/SiO_2/Al$, pigments having this structure being sold by the company DuPont de Nemours; $Cr/MgF_2/Al/MgF_2/Cr$, pigments having this structure being sold under the name Chromaflair by the company Flex; $MoS_2/SiO_2/Al/SiO_2/MoS_2$; $Fe_2O_3/SiO_2/Al/SiO_2/Fe_2O_3$, and $Fe_2O_3/SiO_2/Fe_2O_3/SiO_2/Fe_2O_3$, pigments having these structures being sold under the name Sicopearl by the company BASF; $MoS_2/SiO_2/mica-oxide/SiO_2/MoS_2$; $Fe_2O_3/SiO_2/mica-oxide/SiO_2/Fe_2O_3$; $TiO_2/SiO_2/TiO_2$ and $TiO_2/Al_2O_3/TiO_2$; $SnO/TiO_2/SiO_2/TiO_2/SnO$; $Fe_2O_3/SiO_2/Fe_2O_3$; $SnO/mica/TiO_2/SiO_2/TiO_2/mica/SnO$, pigments having these structures being sold under the name Xirona by the company Merck (Darmstadt). By way of example, these pigments may be the pigments of silica/titanium oxide/tin oxide structure sold under the name Xirona Magic by the company Merck, the pigments of silica/brown iron oxide structure sold under the name Xirona Indian Summer by the company Merck and the pigments of silica/titanium oxide/mica/tin oxide structure sold under the name Xirona Caribbean Blue by the company Merck. Mention may also be made of the Infinite Colors pigments from the company Shiseido. Depending on the thickness and the nature of the various coats, different effects are obtained. Thus, with the $Fe_2O_3/SiO_2/Al/SiO_2/Fe_2O_3$ structure, the colour changes from greenish gold to reddish grey for $SiO_2$ layers of 320 to 350 nm; from red to gold for $SiO_2$ layers of 380 to 400 nm; from violet to green for $SiO_2$ layers of 410 to 420 nm; from copper to red for $SiO_2$ layers of 430 to 440 nm.

Examples of pigments with a polymeric multilayer structure that may be mentioned include those sold by the company 3M under the name Color Glitter.

Examples of liquid-crystal goniochromatic particles that may be used include those sold by the company Chenix and also the product sold under the name Helicone® HC by the company Wacker.

Fillers

A composition in accordance with the invention may also comprise at least one filler other than perlite, of organic or mineral nature, making it possible especially to give it additional matt-effect or covering properties, and/or improved stability with regard to exudation and migration-resistance properties after application.

The term "filler" should be understood to mean colourless or white solid particles of any shape which are in a form that is insoluble and dispersed in the medium of the composition. These particles, of mineral or organic nature, can give body or rigidity to the composition and/or softness and uniformity to the makeup.

The fillers used in the compositions according to the present invention may be in lamellar, globular or spherical form, in the form of fibres or in any other intermediate form between these defined forms.

The fillers according to the invention may or may not be surface-coated, and in particular they may be surface-treated with silicones, amino acids, fluoro derivatives or any other substance that promotes the dispersion and compatibility of the filler in the composition.

Examples of mineral fillers that may be mentioned include talc, mica, silica, hollow silica microspheres, kaolin, calcium carbonate, magnesium carbonate, hydroxyapatite, boron nitride, glass or ceramic microcapsules, and composites of silica and of titanium dioxide, such as the TSG series sold by Nippon Sheet Glass.

Examples of organic fillers that may be mentioned include polyamide powders (Nylon® Orgasol from Atochem), polyethylene powder or polymethyl methacrylate powder, polytetrafluoroethylene (Teflon) powders, powders of acrylic acid copolymers (Polytrap from the company Dow Corning), lauroyllysine, hollow polymer microspheres such as those of polyvinylidene chloride/acrylonitrile, for instance Expancel (Nobel Industrie), hexamethylene diisocyanate/trimethylol hexyl lactone copolymer powder (Plastic Powder from Toshiki), silicone resin microbeads (for example Tospearl from Toshiba), natural or synthetic micronized waxes, metal soaps derived from organic carboxylic acids containing from 8 to 22 carbon atoms and preferably from 12 to 18 carbon atoms, for example zinc stearate, magnesium stearate, lithium stearate, zinc laurate or magnesium myristate, Polypore® L 200 (Chemdal Corporation), and polyurethane powders, in particular crosslinked polyurethane powders comprising a copolymer, the said copolymer comprising trimethylol hexyl lactone. It may in particular be a hexamethylene diisocyanate/trimethylol hexyl lactone polymer. Such particles are especially commercially available, for example, under the name Plastic Powder D400® or Plastic Powder D-800® from the company Toshiki, and mixtures thereof.

According to one embodiment, the compositions according to the invention may comprise, as filler other than perlite, silica, preferably in the form of microspheres. As commercial references of silicas that may be used in the context of the present invention, an example that may be mentioned is the reference Silica Beads SB 700 from Miyoshi, with a mean size of 5 microns.

According to one embodiment, the compositions according to the invention may comprise, as filler other than perlite, polyamide powder, and especially Nylon powder and more particularly Nylon-12 powder. As commercial references of Nylon powders that may be used in the context of the present invention, an example that may be mentioned is Nylon® Orgasol from Arkema, and more particularly Orgasol® 2002 EXD NAT COS (mean particle size of about 10 μm).

According to one embodiment, the compositions according to the invention may comprise, as filler other than perlite, silica, preferably in the form of microspheres, and Nylon powder as defined above.

Additives

A cosmetic composition according to the invention may also comprise any additive usually used in the field under consideration, chosen, for example, from gums, anionic, cationic, amphoteric or nonionic surfactants, silicone surfactants, resins, dispersants, semi-crystalline polymers, antioxidants, essential oils, preserving agents, fragrances, neutralizers, antiseptics, UV-screening agents, cosmetic active agents, such as vitamins, moisturizers, emollients or collagen-protecting agents, and mixtures thereof.

It is a matter of routine operations for a person skilled in the art to adjust the nature and amount of the additives present in the compositions in accordance with the invention such that the desired cosmetic properties and stability properties thereof are not thereby affected.

A cosmetic composition of the invention may be in the form of a skin makeup product, in particular a foundation, a hot-cast foundation product, a body makeup product, a concealer, an eyeshadow or a lipstick. It may be in the form of an anhydrous gel, in the form of a stick or wand, or in the form of a soft paste.

A care composition according to the invention may in particular be an antisun composition or a deodorant.

Preferably, the composition according to the invention is in the form of a fluid foundation.

The present invention also relates to the use, in a cosmetic composition for making up and/or caring for the skin, of perlite and of at least one vinyl polymer bearing at least one carbosiloxane dendrimer-based unit, for increasing the remanence of the matt effect imparted by the said composition.

Matt Effect and Remanence of the Matt Effect

The matt effect and the remanence of the matt effect may be measured by means of the protocol described below.

The matt effect on a region of skin is measured using a polarimetric camera, which is a black and white polarimetric imaging system, with which images are acquired in parallel (P) and crossed (C) polarized light.

By analysing the image resulting from subtraction of the two images (P-C), the gloss is quantified, by measuring the average greyscale of the brightest 5% of pixels corresponding to the gloss areas.

More specifically, the measurements are performed on a panel of individuals, for example a sample of 16 women who wait in an air-conditioned room (22° C.±2° C.) 15 minutes before the start of the test. They remove their makeup and an image of one of their cheeks is acquired with the polarimetric camera. This image allows measurement of the gloss at T0 before applying makeup. Next, about 100 mg of cosmetic composition are weighed out on a watch glass and are applied by naked finger to the half-face on which the measurement at T0 was taken.

After a drying time of 15 minutes, an image of the made-up cheek is acquired with the polarimetric camera. This image allows measurement of the gloss just after applying makeup (Timm). The models then return to the air-conditioned room for 3 hours.

Finally, an image of the made-up cheek after a waiting time of 3 hours is acquired with the polarimetric camera. This image allows measurement of the gloss after 3 hours of makeup (T3h).

The results are expressed by calculating the difference (Timm−T0), which measures the effect of the makeup. A negative value means that the makeup reduces the gloss of the skin and that it thus has a matt effect.

The difference (T3h−Timm) measuring the remanence of this effect is then calculated. The value obtained should be as low as possible, which means that the matt effect of the makeup does not change over time.

The present invention also relates to a cosmetic treatment process comprising the application to the skin of a composition as defined above.

The present invention also relates to a non-therapeutic process for making up and/or caring for the skin, comprising a step of applying to the skin at least one coat of a composition as defined above.

The present invention also relates to a skin makeup process in which a composition as defined above is applied.

EXAMPLES

Influence of the Nature of the Polymer on the Remanence of the Matt Effect

The fluid foundation Examples 1 and 2 make it possible to show that the dendrimer acrylate silicone of the invention affords better remanence of the matt effect than a silicone resin.

Next, phase A2 is added at room temperature, by stirring using a Moritz blender (1000 rpm) until homogenized.

Phase A3 is prepared separately by milling three times in a three-roll mill the mixture of pigments and of cyclohexasiloxane.

This phase A3 is then added, with continued stirring, along with phases A4 and A5.

The aqueous phase B is also prepared separately, by weighing out in a beaker the butylene glycol and the magnesium sulfate, and by adding water preheated to 95° C.

The aqueous phase is stirred using a magnetic bar until homogenized.

The emulsion is prepared at room temperature: the aqueous phase B is poured into the fatty phase while gradually increasing the stirring speed (Moritz blender) up to 4000 rpm. Stirring is continued for 10 minutes.

Phase C (ethanol) is finally added.

The product obtained is stirred using a Rayneri blender (paddles) for 10 minutes between 50 and 60 rpm.

| | | Example 1 (Invention) % mass | Example 2 (comparative) % mass |
|---|---|---|---|
| A1 | Dimethicone copolyol sold under the reference KF 6017 by the company Shin-Etsu | 2.00 | 2.00 |
| | Cetyl PEG/PPG-10/1 dimethicone sold under the reference Abil EM 90 by the company Goldschmidt | 1.00 | 1.00 |
| | Cyclohexasiloxane | 8.20 | 8.20 |
| | Isododecane | 1.00 | — |
| | Isohexadecane | 1.60 | 1.60 |
| | Ethyl hexyl methoxycinnamate | 3.00 | 3.00 |
| A2 | Butyl acrylate copolymer containing dendritic silicone side chains: Tris((trimethylsiloxy)siloxyethyldimethylsiloxy)silylpropyl methacrylate in isododecane (40/60) sold under the reference Dow Corning FA 4002 ID by Dow Corning. | 10.00 | — |
| | Trimethyl siloxysilicate resin sold under the reference SR 1000 by the company Momentive Performance Materials | — | 4.00 |
| | Isododecane | — | 7.00 |
| A3 | Cyclohexasiloxane | 7.50 | 7.50 |
| | Yellow iron oxide coated with aluminium stearoyl glutamate | 2.15 | 2.15 |
| | Red iron oxide mated with aluminium stearoyl glutamate | 0.64 | 0.64 |
| | Black iron oxide coated with aluminium stearoyl glutamate | 0.23 | 0.23 |
| | Titanium dioxide coated with aluminium stearoyl glutamate | 8.98 | 8.98 |
| A4 | Nylon 12 powder sold under the reference Orgasol 2002 EXD NAT COS by the company Arkema | 3.00 | 3.00 |
| | Silica microspheres sold under the reference SB 700 by the company Miyoshi Kasei | 1.00 | 1.00 |
| | Perlite sold under the reference Optimat 2550 OR by the company World Minerals | 0.20 | 0.20 |
| A5 | Fragrance | 0.30 | 0.30 |
| B | Demineralized water | 34.50 | 34.50 |
| | Butylene glycol | 6.00 | 6.00 |
| | Magnesium sulfate | 0.70 | 0.70 |
| C | Ethanol | 8.00 | 8.00 |
| | TOTAL | 100% | 100% |

Procedure Example 1

The constituents of phase A1 are weighed out in the main beaker and are stirred with a Moritz blender (1000 rpm) while maintaining at room temperature.

Procedure Example 2

The constituents of phase A1 are weighed out in the main beaker and are stirred with a Moritz blender (1000 rpm) while maintaining at room temperature.

Phase A2 is prepared beforehand by dispersing the silicone resin in the isododecane with stirring using a Rayneri blender equipped with a deflocculator paddle (about 100 rpm).

Next, phase A2 is added at room temperature, by stirring using a Moritz blender (1000 rpm) until homogenized.

Phase A3 is prepared separately by milling three times in a three-roll mill the mixture of pigments and of cyclohexasiloxane.

This phase A3 is then added, with continued stirring, along with phases A4 and A5.

The aqueous phase B is also prepared separately, by weighing out in a beaker the butylene glycol and the magnesium sulfate, and by adding water preheated to 95° C.

The aqueous phase is stirred using a magnetic bar until homogenized.

The emulsion is prepared at room temperature: the aqueous phase B is poured into the fatty phase while gradually increasing the stirring speed (Moritz blender) up to 4000 rpm. Stirring is continued for 10 minutes.

Phase C (ethanol) is finally added.

The product obtained is stirred using a Rayneri blender (paddles) for 10 minutes between 50 and 60 rpm.

|  | Example 1 (invention) | Example 2 (comparative) |
|---|---|---|
| Nature of the polymer | Butyl acrylate copolymer containing dendritic silicone side chains: Tris((trimethylsiloxy)siloxyethyldimethylsiloxy)silylpropyl methacrylate in isododecane (40/60) sold under the reference Dow Corning FA 4002 ID by Dow Corning. | Trimethyl siloxysilicate resin sold under the reference SR 1000 by the company Momentive Performance Materials |
| Matt effect (Timm-T0) | −3.61 | −4.56 |
| Remanence of the matt effect (T3h-Timm) | 1.26 | 2.78 |

These results show that the dendrimer acrylate silicone of the invention affords better remanence of the matt effect.

Influence of the Nature of the Filler on the Remanence of the Matt Effect

The fluid foundation Examples 1 and 3 make it possible to show that perlite affords better remanence of the matt effect than Nylon powder.

The fluid foundation Examples 1 and 4 make it possible to show that perlite affords better remanence of the matt effect than silica.

The matt effect and the remanence of the matt effect are measured according to the protocol indicated above.

|  |  | Example 1 (Invention) % mass | Example 3 (comparative) % mass | Example 4 (comparative) % mass |
|---|---|---|---|---|
| A1 | Dimethicone copolyol sold under the reference KF 6017 by the company Shin-Etsu | 2.00 | 2.00 | 2.00 |
|  | Cetyl PEG/PPG-10/1 dimethicone sold under the reference Abil EM 90 by the company Goldschmidt | 1.00 | 1.00 | 1.00 |
|  | Cyclohexasiloxane | 8.20 | 8.20 | 8.20 |
|  | Isododecane | 1.00 | 1.00 | 1.00 |
|  | Isohexadecane | 1.60 | 1.60 | 1.60 |
|  | Ethyl hexyl methoxycinnamate | 3.00 | 3.00 | 3.00 |
| A2 | Butyl acrylate copolymer containing dendritic silicone side chains: Tris((trimethylsiloxy)siloxyethyldimethylsiloxy)silylpropyl methacrylate in isododecane (40/60) sold under the reference Dow Corning FA 4002 ID by Dow Corning. | 10.00 | 10.00 | 10.00 |
| A3 | Cyclohexasiloxane | 7.50 | 7.50 | 7.50 |
|  | Yellow iron oxide coated with aluminium stearoyl glutamate | 2.15 | 2.15 | 2.15 |
|  | Red iron oxide coated with aluminium stearoyl glutamate | 0.64 | 0.64 | 0.64 |
|  | Black iron oxide coated with aluminium stearoyl glutamate | 0.23 | 0.23 | 0.23 |
|  | Titanium dioxide coated with aluminium stearoyl glutamate | 8.98 | 8.98 | 8.98 |
| A4 | Nylon 12 powder sold under the reference Orgasol 2002 EXD NAT COS by the company Arkema | 3.00 | 3.20 | 3.00 |
|  | Silica microspheres sold under the reference SB 700 by the company Miyoshi Kasei | 1.00 | 1.00 | 1.20 |
|  | Perlite sold under the reference Optimat 2550 OR by the company World Minerals | 0.20 | — | — |

|  |  | Example 1 (Invention) % mass | Example 3 (comparative) % mass | Example 4 (comparative) % mass |
|---|---|---|---|---|
| AS | Fragrance | 0.30 | 0.30 | 0.30 |
| B | Demineralized water | 34.50 | 34.50 | 34.50 |
|  | Butylene glycol | 6.00 | 6.00 | 6.00 |
|  | Magnesium sulfate | 0.70 | 0.70 | 0.70 |
| C | Ethanol | 8.00 | 8.00 | 8.00 |
|  | TOTAL | 100% | 100% | 100% |

Procedure:
The procedure is identical to that of Example 1.

|  | Example 1 (invention) | Example 3 (comparative) | Example 4 (comparative) |
|---|---|---|---|
| Nature of the filler | Perlite sold under the reference Optimat 2550 OR by the company World Minerals | Nylon 12 powder sold under the reference Orgasol 2002 EXD NAT COS by the company Arkema | Silica microspheres sold under the reference SB 700 by the company Miyoshi Kasei |
| Matt effect (Timm-T0) | −3.61 | −3.37 | −5.05 |
| Remanence of the matt effect (T3h-Timm) | 1.26 | 4.41 | 4.02 |

These results show that perlite affords the best remanence of the matt effect, on one hand in comparison to nylon powder and on the other hand in comparison to silica.

The invention claimed is:

1. Composition comprising a physiologically acceptable medium containing perlite and at least one vinyl polymer bearing at least one carbosiloxane dendrimer-based unit, wherein the vinyl polymer containing at least one carbosiloxane dendrimer-based unit has a molecular side chain containing a carbosiloxane dendrimer structure, and is the product of polymerization of:

(A) from 0 to 99.9 parts by weight of a vinyl monomer; and
(B) from 100 to 0.1 part by weight of a carbosiloxane dendrimer of formula (I) below:

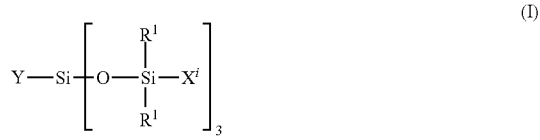

(I)

in which:
R$^1$ represents an aryl group of 5 to 10 carbon atoms or an alkyl group of 1 to 10 carbon atoms;
X$^i$ represents a silylalkyl group which, when i=1, is represented by formula (II):

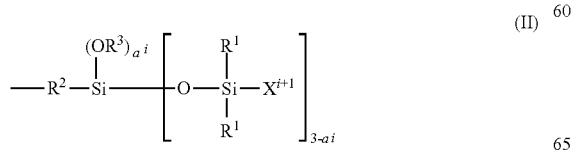

(II)

wherein:
R$^1$ is as defined above in formula (I),
R$^2$ represents an alkylene radical of 2 to 10 carbon atoms,
R$^3$ represents an alkyl group of 1 to 10 carbon atoms,
X$^{i+1}$ is chosen from: a hydrogen atom, an alkyl group of 1 to 10 carbon atoms, an aryl group of 5 to 10 carbon atoms and a silylalkyl group defined above of formula (II) with i=i+1,
i is an integer from 1 to 10 which represents the generation of the said silylalkyl group, and
a$^i$ is an integer from 0 to 3;
Y represents a radical-polymerizable organic group chosen from: organic groups containing a methacrylic group or an acrylic group, the said organic groups being represented by the formulae:

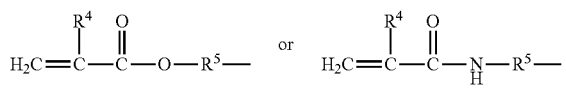

wherein:
R$^4$ represents a hydrogen atom or an alkyl group of 1 to 10 carbon atoms; and
R$^5$ represents an alkylene group of 1 to 10 carbon atoms; and organic groups containing a styryl group of formula:

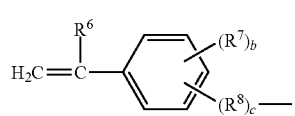

wherein:
R⁶ represents a hydrogen atom or an alkyl group of 1 to 10 carbon atoms;
R⁷ represents an alkyl group of 1 to 10 carbon atoms;
R⁸ represents an alkylene group of 1 to 10 carbon atoms;
b is an integer from 0 to 4; and
c is 0 or 1, such that if c is 0, —(R⁸)$_c$— represents a bond.

2. Composition according to claim 1, wherein the carbosiloxane dendrimer is represented by the following formula:

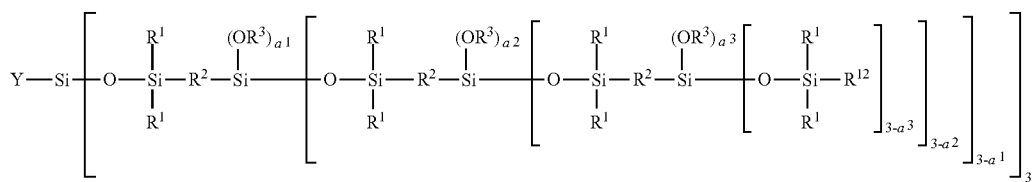

wherien:
each a¹, a² and a³ is individually an integer from 0 to 3; and
R¹² is H, an aryl group of 5 to 10 carbon atoms or an alkyl group of 1 to 10 carbon atoms.

3. Composition according claim 1, wherein the carbosiloxane dendrimer is represented by one of the following formulae:

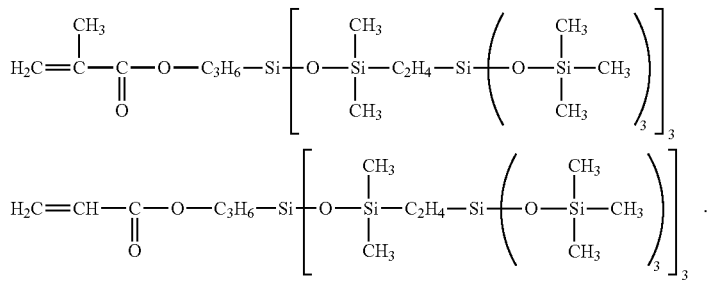

4. Composition according to claim 1, wherein the vinyl polymer bearing at least one carbosiloxane dendrimer-based unit is present in an active material content of from 0.5% to 20% by weight relative to the total weight of the said composition.

5. Composition according to claim 1, wherein the perlite is in the form of particles, at least 50% of the particles of which are smaller than 25 μm in size.

6. Composition according to claim 1, wherein the perlite represents from 0.001% to 15%, by weight relative to the total weight of the said composition.

7. Composition according to claim 1, comprising a fatty phase.

8. Composition according to claim 1 which is, in the form of an emulsion.

9. Composition according to claim 1, comprising a lipophilic structuring agent.

10. Composition according to claim 1, comprising a dyestuff.

11. Composition according to claim 1, comprising a thickener or gelling agent.

12. Composition according to claim 1, in the form of fluid foundation.

13. A method for making up and/or caring for the skin comprising applying to the skin a cosmetic composition of claim 1.

14. Composition according claim 3, wherein the vinyl polymer bearing at least one carbosiloxane dendrimer-based unit is present in an active material content of from 0.5% to 20% by weight relative to the total weight of the said composition.

15. Composition according to claim 3, wherein the perlite is in the form of particles, at least 50% of the particles of which are smaller than 25 μm in size.

16. Composition according to claim 3, wherein the perlite represents from 0.001% to 15%.

17. Composition according claim 1, wherein the vinyl polymer bearing at least one carbosiloxane dendrimer-based unit is present in an active material content of from 2-10% by weight relative to the total weight of the said composition.

18. Composition according to claim 3, wherein the vinyl polymer bearing at least one carbosiloxane dendrimer-based unit is present in an active material content of from 3% to 5% by weight relative to the total weight of the said composition.

19. Composition according to claim 1 comprising from 0.001% to 15% of perlite and 0.5% to 20% of at least one vinyl polymer bearing at least one carbosiloxane dendrimer-based unit, wherein the percentages are by weight relative to the total weight of said composition.

* * * * *